United States Patent
Stewart et al.

(10) Patent No.: US 12,163,945 B2
(45) Date of Patent: Dec. 10, 2024

(54) AUTOMATED ANALYSIS OF DRILLING FLUID

(71) Applicants: M-I L.L.C., Houston, TX (US); SCHLUMBERGER NORGE AS, Stavanger (NO)

(72) Inventors: Colin Stewart, Houston, TX (US); Zakhar Chizhov, Katy, TX (US); Jerry Thomas Connaughton, Houston, TX (US); Neil McPherson, Aberdeen (GB); Truls Fossdal, Stavanger (NO); Rahul Sheladia, Katy, TX (US); Ragnar Melz, Sandnes (NO)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 85 days.

(21) Appl. No.: 16/578,570

(22) Filed: Sep. 23, 2019

(65) Prior Publication Data

US 2021/0088499 A1    Mar. 25, 2021

Related U.S. Application Data

(63) Continuation-in-part of application No. PCT/US2018/040769, filed on Jul. 30, 2018.
(Continued)

(51) Int. Cl.
*G01N 33/28* (2006.01)
*E21B 49/08* (2006.01)
(Continued)

(52) U.S. Cl.
CPC ....... *G01N 33/2823* (2013.01); *E21B 49/088* (2013.01); *G01N 11/14* (2013.01);
(Continued)

(58) Field of Classification Search
CPC ...... G01N 33/2823; G01N 11/14; G01N 1/14; G01N 1/4022; G01N 11/00;
(Continued)

(56) References Cited

U.S. PATENT DOCUMENTS 4,273,650 A    6/1981 Solomon
6,240,770 B1   6/2001 Raffer
(Continued)

FOREIGN PATENT DOCUMENTS

CN    2783315 Y    5/2006
CN    101842679 A  9/2010
(Continued)

OTHER PUBLICATIONS

International Search Report and Written Opinion for the cross referenced International patent application PCT/US2018/040769 dated Oct. 25, 2018.
(Continued)

*Primary Examiner* — Harshad R Patel
*Assistant Examiner* — Gedeon M Kidanu
(74) *Attorney, Agent, or Firm* — Jeffrey D. Frantz

(57) ABSTRACT

A system includes a fluid conduit, a fluid chamber in communication with the fluid conduit, a rheology sensor in communication with the fluid chamber, and an electric temperature controller in communication with the fluid chamber. The fluid chamber is cooled or heated in response to a first control signal from the electric temperature controller.

16 Claims, 11 Drawing Sheets

Related U.S. Application Data

(60) Provisional application No. 62/529,454, filed on Jul. 6, 2017.

(51) Int. Cl.
*G01N 11/14* (2006.01)
*G01F 1/74* (2006.01)
*G01N 9/36* (2006.01)

(52) U.S. Cl.
CPC ............ *E21B 49/0875* (2020.05); *G01F 1/74* (2013.01); *G01N 9/36* (2013.01)

(58) Field of Classification Search
CPC . G01N 2011/0093; G01N 2035/00376; G01N 2035/00425; G01N 21/0332; G01N 2203/0094; G01N 2203/0676; G01N 27/3271; G01N 7/10; G01N 9/00; G01N 9/36; G01F 1/684; G01F 1/6842; G01F 1/69; G01F 1/696; B09C 1/002; B09C 1/007; Y10S 210/923
See application file for complete search history.

(56) References Cited

U.S. PATENT DOCUMENTS

| | | | |
|---|---|---|---|
| 6,257,354 | B1 | 7/2001 | Schrader et al. |
| 6,330,826 | B1 | 12/2001 | Meeten |
| 6,584,833 | B1 | 7/2003 | Jamison et al. |
| 6,931,916 | B2 | 8/2005 | Zamora et al. |
| 8,387,442 | B2 | 3/2013 | Jamison et al. |
| 8,784,745 | B2 * | 7/2014 | Nelson ................ C12Q 1/6844 422/198 |
| 9,134,291 | B2 * | 9/2015 | Jamison .................. E21B 21/00 |
| 9,194,972 | B2 | 11/2015 | Van Der Zwaag |
| 9,222,351 | B2 | 12/2015 | Jamison |
| 9,428,976 | B2 | 8/2016 | Porter et al. |
| 9,513,203 | B2 | 12/2016 | Kulkarni et al. |
| 9,777,542 | B2 | 10/2017 | Stock et al. |
| 2003/0084708 | A1 | 5/2003 | Abnett |
| 2003/0233867 | A1 | 12/2003 | Hall |
| 2006/0175547 | A1 | 8/2006 | DiFoggio et al. |
| 2006/0243047 | A1 | 11/2006 | Terabayashi et al. |
| 2008/0066537 | A1 * | 3/2008 | Hegeman ................ E21B 43/25 73/152.28 |
| 2009/0151426 | A1 | 6/2009 | Shah |
| 2010/0304418 | A1 | 12/2010 | Moussavi et al. |
| 2012/0094876 | A1 | 4/2012 | Jamison et al. |
| 2013/0009784 | A1 | 1/2013 | Villard et al. |
| 2013/0277113 | A1 * | 10/2013 | Murphy ................ E21B 21/065 175/46 |
| 2013/0312511 | A1 | 11/2013 | Jamison et al. |
| 2014/0096930 | A1 | 4/2014 | Krug, Jr. |
| 2014/0105446 | A1 | 4/2014 | Maxey et al. |
| 2014/0166361 | A1 | 6/2014 | Jamison et al. |
| 2014/0202772 | A1 | 7/2014 | Kulkarni et al. |
| 2014/0319080 | A1 * | 10/2014 | Kaarigstad .............. E21B 49/00 210/342 |
| 2015/0233614 | A1 * | 8/2015 | Kindt .................... G01N 25/145 62/3.3 |
| 2015/0316527 | A1 * | 11/2015 | Stock ...................... E21B 47/00 73/54.16 |
| 2016/0040533 | A1 * | 2/2016 | Harrison ............... E21B 49/081 73/152.05 |
| 2016/0138395 | A1 | 5/2016 | Kulkarni et al. |
| 2016/0265029 | A1 | 9/2016 | Ying et al. |
| 2016/0313292 | A1 | 10/2016 | Desai et al. |
| 2016/0356919 | A1 | 12/2016 | Jamison et al. |
| 2017/0038491 | A1 | 2/2017 | Gonzalez et al. |
| 2017/0198189 | A1 | 7/2017 | Panamarathupalayam |
| 2018/0164201 | A1 | 6/2018 | Zimmer et al. |
| 2018/0266930 | A1 | 9/2018 | Nowak et al. |
| 2020/0124513 | A1 | 4/2020 | Gao et al. |
| 2020/0182852 | A1 | 6/2020 | Stewart et al. |
| 2023/0149867 | A1 | 5/2023 | Smith |

FOREIGN PATENT DOCUMENTS

| | | | | |
|---|---|---|---|---|
| CN | 102187199 | A | 9/2011 | |
| CN | 203025064 | U | 6/2013 | |
| CN | 106092976 | A | 11/2016 | |
| CN | 106415236 | A | 2/2017 | |
| CN | 107780858 | A | 3/2018 | |
| CN | 209109371 | U | 7/2019 | |
| GB | 1379470 | A | 1/1975 | |
| GB | 2344180 | A | 5/2000 | |
| JP | H1078824 | A | 3/1998 | |
| JP | 2003083859 | A | 3/2003 | |
| JP | 2007086035 | A * | 4/2007 | |
| KR | 20110075086 | A | 7/2011 | |
| WO | 0167068 | A2 | 9/2001 | |
| WO | WO-2009079059 | A1 * | 6/2009 | ............. E21B 47/10 |
| WO | WO-2011100435 | A2 * | 8/2011 | ............. E21B 21/01 |
| WO | 2015191091 | A1 | 12/2015 | |

OTHER PUBLICATIONS

International Search Report and Written Opinion issued in International Patent Application No. PCT/US2020/045183 dated Nov. 24, 2020, 13 pages.

International Preliminary Report on Patentability issued in Intentional Patent Application No. PCT/US2018/040769 dated Jan. 7, 2020, 5 pages.

Search and Examination report issued in European Patent Application 18827666.1 dated Feb. 11, 2021, 14 pages.

Garma Electronica s.l, Advantages of Thermal Dispersion Level Switch, Retrieved from the internet: URL: https://www.https://www.garmasl.com/en/blog/82-advantages-of-thermal-dispersion-level-switch, Published Nov. 8, 2016, retrieved on Feb. 1, 2021, 2 pages.

API 13B-1 Standard, "Recommended Practice for Field Testing Water-based Drilling Fluids," Fourth Edition, Mar. 2009, Errata 1, Aug. 2014, 104 pages.

API 13B-2 Standard, "Recommended Practice for Field Testing Oil-based Drilling Fluids," Fifth Edition, Apr. 2014, Errata 1, Aug. 2014, 154 pages.

Fann Instrument Company, Model 35 Viscometer Instruction Manual, Houston, Texas, 2016, 45 pages.

English Translation of JP-H1078824-A (Year: 1998).

Office Action issued in U.S. Appl. No. 16/623,383 dated Dec. 27, 2021, 17 pages.

Search Report and Writen Opinion of Russian Patent Application No. 2020104983 dated Jan. 21, 2022, 16 pages with English translation.

Exam Report issued in India Patent Application No. 202017001853 dated Feb. 28, 2022, 5 pages.

International Preliminary Report on Patentability issued in International Patent Application No. PCT/US2020/045183 on Apr. 7, 2022, 10 pages.

Saasen, et al., Prediction of Barite Sag Potential of Drilling Fluids From Rehological Measurements, Society of Petrouleum Engineers, SPE-29410 (1995).

Office Action issued in U.S. Appl. No. 16/656,491 dated Mar. 10, 2022, 10 pages.

First Office Action issued in Chinese Patent Application No. 2018800443773 dated Apr. 26, 2022, 26 pages with English translation.

Preliminary Office Action issued in Brazil Patent Application No. BR112019028218-1 dated Aug. 4, 2022, 6 pages with English translation.

Nagy, M. J. et al., "The Effect of Pulse Width Modulation (PWM) Frequency on the Reliability of Thermoelectric Modules", IEEE presented at the 18th International Conference on Thermoelectrics, Piscataway, New Jersey, U.S.A., 1999, pp. 123-125.

Communication Pursuant to Article 94(3) issued in European Patent Application No. 18827666.1 dated Aug. 22, 2022, 9 pages.

Decision on Grant issued in Russian Patent Application No. 2020104983 dated Sep. 22, 2022, 19 pages with English translation.

Office Action issued in Colombia Patent Application NC2020/0001163 dated Sep. 26, 2022, 28 pages with English translation.

(56) References Cited

OTHER PUBLICATIONS

Exam Report issued in Kuwait Patent Application No. KW/P/2019/433 dated May 16, 2022, 4 pages.
Second Office Action issued in Chinese Patent Application No. 2018800443773 dated Jan. 25, 2023, 25 pages with English translation.
Written Opinion issued in Brazilian patent application 1120190282181 dated Feb. 7, 2023, 11 pages with English translation.
Exam Report under Section 18(3) issued in United Kingdom Patent Application No. GB2204086.9 dated Mar. 7, 2023, 4 pages.
First Office Action issued in Mexico Patent Application No. MX/a/2020/000181 dated Mar. 29, 2023, 10 pages.
Office Action issued in Colombia Patent Application NC2020/0001163 dated Apr. 27, 2023, 29 pages.
Exam Report No. 1 issued in Australia Patent Application No. 2018298054 dated Apr. 15, 2023, 3 pages.
Substantive Exam issued in Saudi Arabia Patent Application No. 522432037 dated May 18, 2023, 15 pages.
Decision of Rejection issued in China Patent Application No. 201880044377.3 dated May 26, 2023, 23 pages.
Substantive Exam issued in Saudi Arabia Patent Application No. 520410938 dated Mar. 30, 2023, 29 pages.
Office Action issued in Colombia Patent Application No. NC2020/0001163 dated Nov. 14, 2023, 32 pages with English translation.
Office Action issued in U.S. Appl. No. 17/980,819 dated Dec. 21, 2023, 21 pages.
Examination Report issued in Great Britain Patent Application No. GB2204086.9 on Oct. 6, 2023; 3 pages.
Hearing Notice issued in India Patent Application No. 202017001853 dated Feb. 26, 2024, 6 pages.
Office Action issued in U.S. Appl. No. 17/980,819 dated Apr. 4, 2024, 15 pages.
Examination Report issued in Malaysian Patent Application PI2020000051 on Mar. 25, 2024, 4 pages.
Office Action and Search Report issued in UAE Patent Application P6000023/2020 on Oct. 30, 2023, 9 pages.
2nd Exam Report issued in Saudi Arabia Patent Application No. 520410938 dated Oct. 12, 2023, 30 pages.

\* cited by examiner

AUTOMATED ANALYSIS OF DRILLING FLUID

CROSS-REFERENCE TO RELATED APPLICATIONS

This application is a continuation-in-part of International Application No. PCT/2018/040769, filed Jul. 3, 2018, which claims the benefit of U.S. Provisional Application No. 62/529,454, filed Jul. 6, 2017. Each patent application identified above is incorporated by reference in its entirety.

BACKGROUND

Drilling fluids are pumped to a center of a downhole drill string when drilling a wellbore. The drilling fluids travel down the drill string and exit the drill string at a drill bit through nozzles. The drilling fluids then enter an annulus of the wellbore and return to the drilling equipment located at the surface. The drilling fluids provide lubrication and cooling of components during the drilling process. The drilling fluids also carry cuttings out of the wellbore, control wellbore pressure, and perform a number of other functions in connection with drilling the wellbore. To ensure that the properties of the drilling fluids are adequate, an engineer consistently checks the properties of the drilling fluids. For example, the viscosity of the drilling fluids must be high enough to carry the cuttings out of the wellbore, while at the same time be low enough to allow the cuttings and entrained gas to escape the drilling fluids at the surface. Depending on the operation, the engineer may check the properties of the drilling fluids several times in a twenty-four (24) hour period.

Conventional fluid analyzers have several drawbacks in connection with their use. For example, conventional fluid analyzers have limits of operation that do not allow for analysis of particularly gelatinous fluids. When conventional fluid analyzers are used in such situations, the internal pump used for transporting the drilling fluid becomes overworked and fails. In response to this failure, conventional fluid analyzers must be disassembled to clean the interior components.

There is a need to provide a fluid analyzer that will automatically analyze fluids without constant attention from a technician, and wherein the fluid analyzer may provide rheology parameters for particularly gelatinous fluids.

SUMMARY

So that the manner in which the above recited features of the present disclosure can be understood in detail, a more particular description of the disclosure, briefly summarized below, may be had by reference to embodiments, some of which are illustrated in the drawings. It is to be noted that the drawings illustrate only typical embodiments of this disclosure and are therefore not to be considered limiting of its scope, for the disclosure may admit to other equally effective embodiments without specific recitation. Accordingly, the following summary provides just a few aspects of the description and should not be used to limit the described embodiments to a single concept.

In an embodiment, a testing apparatus is disclosed. The testing apparatus may comprise a fluid collection container configured to hold a drilling fluid and a first fluid conduit connected to the fluid collection volume. The testing apparatus may also comprise a second fluid conduit connected to the fluid collection volume and a fluid chamber configured to receive drilling fluid from both the first fluid conduit and the second fluid conduit. The testing apparatus may also comprise a first pump configured to move the drilling fluid from the fluid collection volume to the fluid chamber, the first pump connected to the first fluid conduit and a second pump configured to move the drilling fluid from a bottle to the fluid chamber, the second pump connected to the second fluid conduit. The testing apparatus may also comprise a rheology sensor in communication with the fluid chamber and a user interface configured to accept user defined data. The testing apparatus may also comprise an electrical system connected to the user interface and configured to process the user defined data, wherein the testing apparatus is configured to receive user data on tests to be performed by the testing apparatus, and control the first pump, the second pump and the rheology sensor to automatically test the drilling fluid according to the user defined data.

In another embodiment, a method for automatic testing fluid samples is disclosed. The method may comprise supplying a drilling fluid sample into a fluid chamber through action of at least two pumps and receiving instructions to test the drilling fluid sample for at least two temperatures. The method may also provide for automatically adjusting a temperature of the drilling fluid sample to a first temperature of the at least two temperatures and testing the fluid sample at the first temperature. The method may also provide for automatically adjusting the temperature of the drilling fluid sample to a second temperature of the at least two temperatures and testing the fluid sample at the second temperature.

In another embodiment, a testing apparatus is disclosed. The testing apparatus may comprise a fluid collection container configured to hold a drilling fluid. The testing apparatus may also comprise a first fluid conduit connected to the fluid collection volume. The testing apparatus may also comprise a second fluid conduit connected to the fluid collection volume. The testing apparatus may also comprise a fluid chamber configured to receive drilling fluid from the fluid conduit. The testing apparatus may also comprise a first pump configured to move the drilling fluid from the bottle to the fluid chamber. The testing apparatus may also comprise a second pump configured to move the drilling fluid from the bottle to the fluid chamber. The testing apparatus may also comprise a rheology sensor in communication with the fluid chamber and a user interface configured to accept user defined data. The testing apparatus may also comprise an electrical system connected to the user interface and process the user defined data, wherein the testing apparatus is configured to receive user data, and control the first pump, the second pump and the rheology sensor to automatically test the drilling fluid according to the user defined data, the electrical system further configured with a memory to store and transmit data related to parameters of a tested fluid. The testing apparatus may also comprise at least two fans configured to move a volume of air and at least one equipment thermometer connected to at least one of the rheology sensor, the first pump and the second pump. The testing apparatus may also comprise a housing configured to house the first pump, the second pump, the rheology sensor, the user interface, the electrical system, the at least one equipment thermometer and the at least two fans.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the drawings. It is to be noted, however, that the appended drawings illustrate only typical embodiments of this disclosure and are therefore not be considered limiting of its scope, for the disclosure may admit to other equally effective embodiments.

Figure 1:
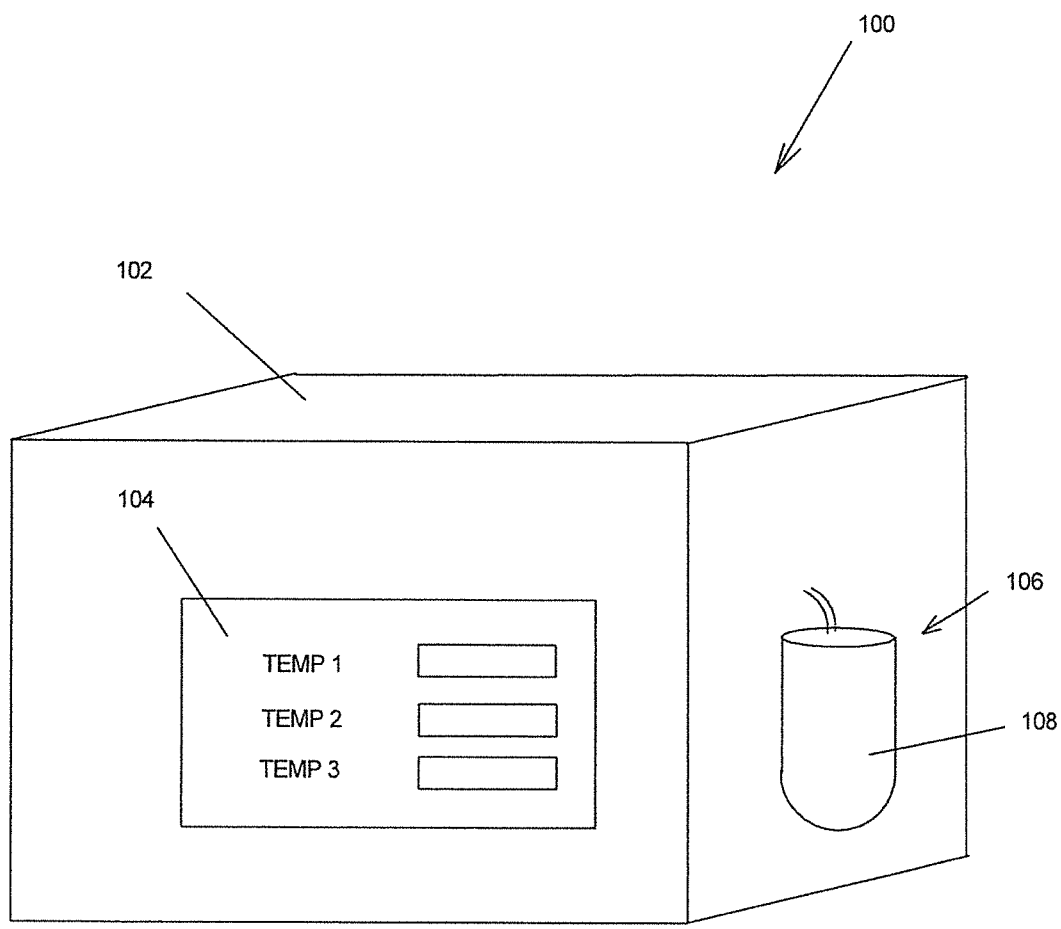
FIG. 1 depicts a perspective view of an example fluid testing apparatus in accordance with the present disclosure.

While the embodiments described herein are susceptible to various modifications and alternative forms, specific embodiments have been shown by way of example in the drawings and will be described in detail herein. The embodiments described herein are not intended, however, to be limited to the particular forms disclosed. Rather, the instant disclosure covers all modifications, equivalents, and alternatives falling within the scope of the appended claims.

DETAILED DESCRIPTION

In the following, reference is made to embodiments of the disclosure. It should be understood, however, that the disclosure is not limited to specific described embodiments. Instead, any combination of the following features and elements, whether related to different embodiments or not, is contemplated to implement and practice the disclosure. Furthermore, although embodiments of the disclosure may achieve advantages over other possible solutions and/or over the prior art, whether or not a particular advantage is achieved by a given embodiment is not limiting of the disclosure. Thus, the following aspects, features, embodiments and advantages are merely illustrative and are not considered elements or limitations of the claims except where explicitly recited in a claim. Likewise, reference to "the disclosure" shall not be construed as a generalization of inventive subject matter disclosed herein and shall not be considered to be an element or limitation of the claims except where explicitly recited in a claim.

Although the terms first, second, third, etc., may be used herein to describe various elements, components, regions, layers and/or sections, these elements, components, regions, layers and/or sections should not be limited by these terms. These terms may be only used to distinguish one element, component, region, layer or section from another element, component, region, layer or section. Terms such as "first", "second" and other numerical terms, when used herein, do not imply a sequence or order unless clearly indicated by the context. Thus, a first element, component, region, layer or section discussed herein could be termed a second element, component, region, layer or section without departing from the teachings of the example embodiments.

When an element or layer is referred to as being "on," "engaged to," "connected to," or "coupled to" another element or layer, it may be directly on, engaged, connected, coupled to the other element or layer, or interleaving elements or layers may be present. In contrast, when an element is referred to as being "directly on," "directly engaged to," "directly connected to," or "directly coupled to" another element or layer, there may be no interleaving elements or layers present. Other words used to describe the relationship between elements should be interpreted in a like fashion. As used herein, the term "and/or" includes any and all combinations of one or more of the associated listed terms.

Some embodiments will now be described with reference to the figures. Like elements in the various figures will be referenced with like numbers for consistency. In the following description, numerous details are set forth to provide an understanding of various embodiments and/or features. It will be understood, however, by those skilled in the art, that some embodiments may be practiced without many of these details, and that numerous variations or modifications from the described embodiments are possible. As used herein, the terms "above" and "below", "up" and "down", "upper" and "lower", "upwardly" and "downwardly", and other like terms indicating relative positions above or below a given point are used in this description to more clearly describe certain embodiments.

Drilling fluid is circulated down the drill string, out nozzles located in the drill bit, and up an annulus of a wellbore. The drilling fluid can be used to remove cuttings from the bottom of the wellbore. The physical properties of the drilling fluid are monitored during a drilling operation to determine whether the drilling fluid is working adequately and to make any desired changes as drilling progresses. Drilling fluid that is circulated through the wellbore and drilling apparatus may be defined as "drilling mud". Drilling fluids may have different physical characteristics to perform different functions. Aspects of the disclosure presented herein provide apparatus and methods that provide a capability to automatically test the physical characteristics of drilling fluids that have a high viscosity that cannot be tested by conventional apparatus.

The drilling fluid may be tested to determine or measure physical characteristics of the drilling fluid, such as testing rheology. Rheology tests may be performed with a rheology meter, such as a viscometer, a rheometer, or other type of sensor. These tests may be performed at the well site, such as in a mobile laboratory. The fluid testing apparatus 100 depicted in FIG. 1, may complete a series of tests on the drilling fluid sequentially without further instructions from the user between tests. Other types of fluid property tests that may be performed with the fluid testing apparatus 100 include taking measurements of the drilling fluid weight, rheology, density, water-oil content, emulsion electrical stability, fluid conductivity, and particle size distribution. Based on the principles described in the present disclosure, a fluid testing apparatus 100 may perform at least one or more of the fluid property tests automatically. These automatic tests may occur at temperatures that are different or similar to the temperature of the drilling fluid progressing through the wellbore and drilling apparatus.

The fluid testing apparatus 100 may include a housing 102, a user interface 104, and a bottle receiver 106. A drilling fluid sample may be collected from the circulating drilling fluid within the drilling system or from another location into a bottle 108. Although described as a bottle 108, other configurations may be defined as a fluid collection container that has an outside surface and an inside volume used for storage of drilling fluid. The collection of the drilling fluid may be automatically accomplished through the use of pumps, as an example. The bottle 108 may be connected to the bottle receiver 106. A fluid conduit may be suspended from the bottle receiver 106 and be submerged into the drilling fluid sample as the bottle 108 is connected to the bottle receiver 106. A pump 200 may actively convey at least a portion of the drilling fluid sample out of the bottle 108 into the fluid testing apparatus 100 where the tests may be performed. As will be described, a single pump system may be used, as disclosed in FIG. 2, as well as a two-pump system, as described in FIG. 9.

The bottle 108 may be secured to the bottle receiver 106 through an interface. In some embodiments, the bottle receiver 106 has an internal thread that can be engaged with an external thread of the bottle 108. In other embodiments, the bottle 108 is snapped into place, held in place through compression, otherwise interlocked with the bottle receiver 106, or otherwise connected to the bottle receiver 106 through another type of attachment. The bottle 108 may be insulated to maintain a constant temperature for testing, in some embodiments. The bottle 108 may also be clear or semi-transparent to allow technicians or engineers to identify the amount of drilling fluid placed within the bottle. The bottle 108 may have gradations on the side to allow technicians or engineers the ability to visually identify the amount of volume present within the bottle 108 that is being tested.

The user interface 104 may allow the user to instruct the fluid testing apparatus 100 to perform desired tests. In some examples, the fluid testing apparatus 100 presents options for testing the drilling fluid sample through the user interface 104. In some examples, the user may indicate the types of tests to be performed as well as the parameters for performing those types of tests. For example, the user may instruct the fluid testing apparatus 100 to perform a viscosity test at multiple temperatures through the user interface 104. The user may also specify the desired temperatures for those tests through the user interface 104. In other embodiments, the user may specify an amount of time that the tests are conducted within.

Any type of user interface 104 may be used in accordance with the principles described in the present disclosure. In some embodiments, the user interface 104 is a touch screen component that is accessible from the housing 102. In this embodiment, a user may interact with the touch screen to input information and provide instructions to the fluid testing apparatus 100. In other embodiments, the fluid testing apparatus 100 may include a wireless receiver where the user can provide information and/or send instructions wirelessly to the fluid testing apparatus 100. For example, the user may send the information and/or provide the instructions with a mobile device, an electronic tablet, a laptop computer, a networked device, a desktop computer, a computing device, another type of device, or combinations thereof. In examples where the user can communicate with the fluid testing apparatus 100 wirelessly, the user may be located onsite or the user may be located at a location that is remote from the vicinity of the wellbore. In some embodiments, an engineer may be located at a remote location, and a local technician may fill the bottle 108 for the engineer so that the engineer does not have to be onsite to evaluate the drilling fluid and make recommendations. In another example embodiment, the user interface may include a keyboard, a mouse, a button, a dial, a switch, a slider, another type of physical input mechanism, or a speaker for voice operated commands or combinations of the above to assist the user to input information or provide instructions to the fluid testing apparatus 100. In some cases, the fluid testing apparatus 100 may include a camera that will allow the user to communicate with motion/hand gestures with the fluid testing apparatus 100.

After inputting the information and instructing the fluid testing apparatus 100 to initiate the tests, the fluid testing apparatus 100 may complete the tests without further involvement from the user. The fluid testing apparatus 100 may automatically transition from one type of test to another as tests are completed. Further, the fluid testing apparatus 100 may automatically adjust the temperature of the drilling fluid sample between tests without involvement from the user. Often, the drilling fluid is tested after circulating through the drill string in a hot, downhole environment. In those circumstances, where the drilling fluid is desired to be tested at a temperature lower than the current temperature of the drilling fluid, the drilling fluid is cooled before the test is performed. The fluid testing apparatus 100 may lower the drilling fluid sample's temperature and free the user to perform other tasks.

Figure 2:
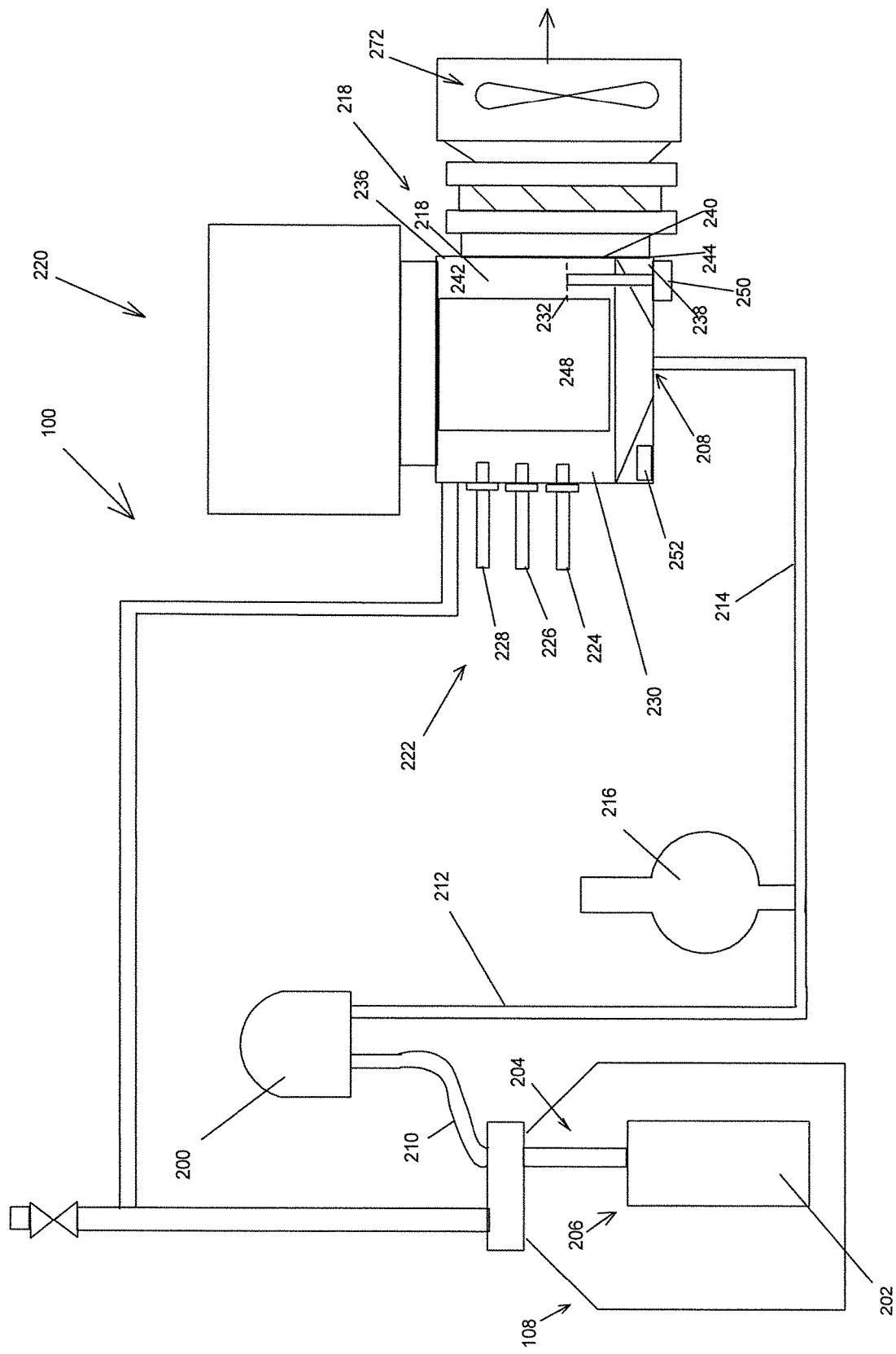
FIG. 2 depicts a schematic of an example of internal components of a fluid testing apparatus in accordance with the present disclosure.
Figure 3:
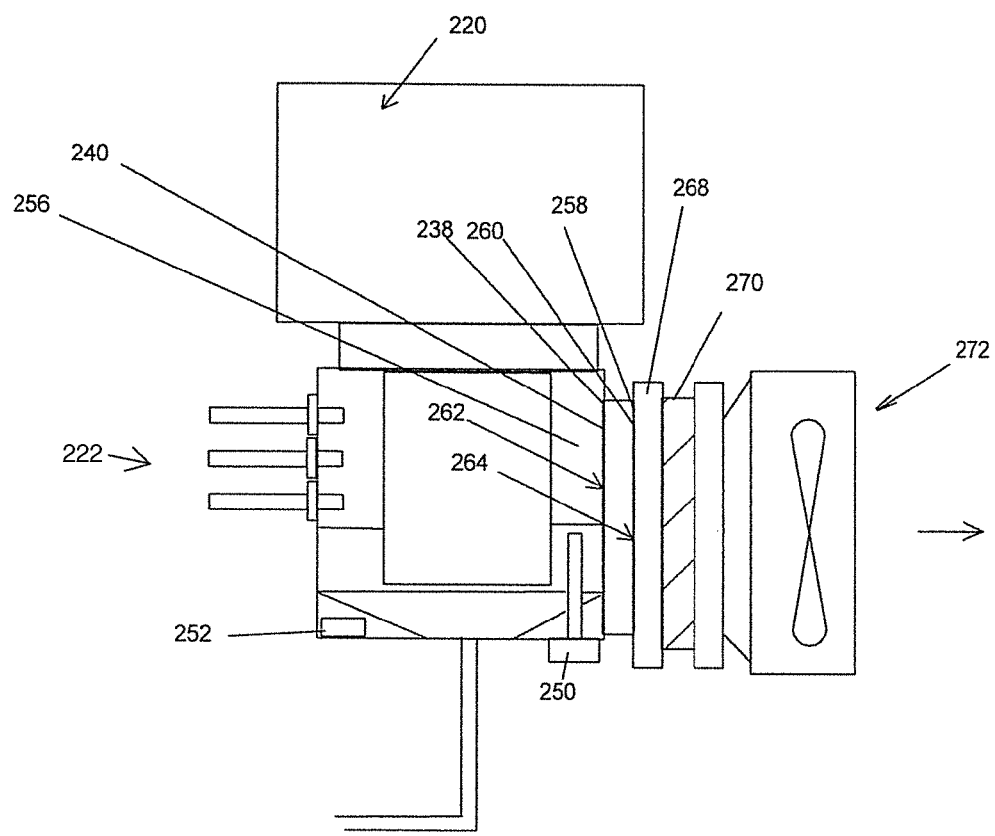
FIG. 3 depicts a detailed view of a fluid chamber of the fluid testing apparatus in accordance with the present disclosure.

FIGS. 2 and 3 depict a schematic of an example of internal components of a fluid testing apparatus 100 in accordance with the present disclosure. FIG. 3 details a portion of the internal components depicted in FIG. 2. In this example, the fluid testing apparatus 100 includes a bottle receiver 106, a pump 200, a fluid conduit 204, a density sensor 216 connected to the fluid conduit 204, a fluid chamber 218 and a rheology sensor 220 connected to the fluid chamber 218.

The bottle receiver 106 may be any appropriate attachment to the exterior of the fluid testing apparatus 100 to which the bottle 108 may be connected and which includes a mechanism for moving the drilling fluid sample 230 from the bottle 108. In the depicted example, a portion of the fluid conduit 204 is suspended from the bottle receiver 106 at a distance so that the inlet 206 is submerged within the drilling fluid sample 230 when the bottle 108 is attached. A filter 202 is connected to the drilling fluid conduit 204 and surrounds the inlet 206 so that solid particles and/or unwanted debris is prevented from entering the fluid conduit 204.

A first portion 210 of the fluid conduit 204 connects the inlet 206 to a pump 200. The pump 200 may be used to pull at least a portion of the drilling fluid sample 230 from the bottle 108 into fluid conduit 204. In some examples, the pump 200 is a peristaltic pump, however, any appropriate type of pump may be used in accordance with the principles described in the present disclosure.

A second portion 212 of the fluid conduit 204 may connect the fluid conduit 204 to the pump 200 and a density sensor 216. In some cases, the pump 200 is at a higher elevation than the density sensor 216. With this type of example, the pump 200 may release the drilling fluid sample 230 and allow gravity to push the drilling fluid sample 230 to the density sensor 216. In other examples, the pump 200 may actively push the drilling fluid sample 230 through the density sensor 216.

Any appropriate type of density sensor 216 can be used. In one example, the density sensor 216 may be a Coriolis density meter that measures a characteristic of the drilling fluid sample 230 as the fluid passes through it. Coriolis density meters may measure the movement/vibrations of internal components of the density meter. These movements may be measured as the drilling fluid sample 230 passes through the density sensor 216. This frequency correlates to the drilling fluid sample's density. In one or more embodiments described, the density sensor 216 may be a Rheonik Model RHM 04.

A third portion 214 of the fluid conduit 204 connects the fluid conduit 204 from the density sensor 216 to a fluid chamber 218. The fluid chamber 218 may include a chamber wall 236 that defines an opening 242. An outlet 208 of the fluid chamber 218 terminates in the opening 242 of the fluid chamber 218 and directs the drilling fluid sample 230 into the fluid chamber 218.

A level detection sensor 222 may send a signal to the pump 200 to stop pumping in the drilling fluid sample 230 when the fluid level 232 is at an appropriate height. Any appropriate type of level detection sensor 222 may be used. A non-exhaustive list of level detection sensors that may be used include ultrasonic sensors, fluid conductivity sensors, capacitance sensors, induction sensors, microwave sensors, laser sensors, float switches, thermal flow switches, hydrostatic pressure sensors, radar-based sensors, magneto restrictive sensors, optical sensors, load cell sensors, other time-of-flight, or combinations thereof.

While each of the above level detection sensors may be used in some applications, some of the above mentioned level detection sensors may not be as effective as other types of sensors for certain types of drilling fluids. In some examples, if a thermal dispersion level detection sensor is incorporated into the fluid chamber 218, the sensor may be effective for a wide variety of different types of drilling fluids. The thermal dispersion level detection sensor can be effective for determining the level of fluids regardless of fluid dielectric strength, tendency to create optical disturbances, and other characteristics of drilling fluids that make level detection challenging.

In one or more embodiments, thermal dispersion technology may be used to measure characteristics of a fluid's flow rate. Generally, fluids are cooler when flowing then when in a static condition. Conventionally, thermal dispersion technology analyzes the temperature of the fluid to determine the flow rate or another characteristic of the fluid. An example where thermal dispersion technology is used in the fluid testing apparatus 100 may be to determine a fluid level 232.

Level detection with thermal dispersion technology may be accomplished by actively moving the drilling fluid sample 230 as the fluid enters into the fluid chamber 218 and measuring temperature differences at various heights along the fluid chamber 218. In some examples, a rotor 248 may cause the drilling fluid sample 230 to rotate within the fluid chamber 218 as the fluid chamber 218 fills. The rotation of the drilling fluid sample 230 caused by the rotor 248 may create a cooling effect on the portions of the chamber wall 236 in direct contact with the fluid. A fluid level 232 may be determined by comparing the temperatures along the fluid chamber's wall and identifying the fluid level 232 at the height where the temperature difference occurs.

In the example of FIGS. 2 and 3, the level detection sensor 222 includes a first level detector 224, a second level detector 226, and a third level detector 228. In some cases, each of the first level detector 224, second level detector 226, and third level detector 228 are thermal dispersion level detectors. In other examples, at least one of those detectors is a different type of sensor. For those level detectors that are thermal level detectors, each may include two or more level thermometers that detect the temperature of the chamber wall 236, the temperature adjacent to the exterior of the chamber wall 236, the temperature adjacent to the interior of the chamber wall 236, or combinations thereof. Each of the level thermometers of the level detector may be adjacent to each other, but at different heights. When the lower of the two thermometers is a different temperature than the higher thermometer, the level detector may send a signal to stop the pump 200. This temperature difference may indicate that the fluid level 232 is between the lower and higher thermometers.

The second level detector 226 may be used as a backup if the first level detector 224 fails to operate properly in this situation; the second level detector 226 may cause a signal to be sent to stop the pump 200.

The third level detector 228 may be used to indicate the fluid level 232 is too high. In some examples, a rheology sensor 220 is placed where other components of the fluid testing apparatus 100 are incorporated into the fluid chamber 218 above the operating fluid level 232. If the fluid level 232 gets too high, the drilling fluid sample 230 may get into these components and interfere with their operation. In one such example, rotary bearings may be above the operating fluid level 232 in the fluid chamber 218, and if the fluid level 232 exceeds the fluid operating level, the drilling fluid sample 230 may get into the rotary bearings. In some cases, the viscometer has rotary bearings that are finely tuned to obtain precise measurement readings. Drilling fluid in these finely tuned bearings can cause the viscometer's measurement outputs to be inaccurate. When activated, the third level detector 228 may cause a message to be communicated to the user that the equipment needs to be checked before proceeding with the tests. In some examples, the third level detector 228 may also send a signal to stop the pump 200.

In the example of FIGS. 2 and 3, the rheology sensor 220 is viscometer. An example viscometer used in all of the embodiments described may be a Grace Instrument Company M3600 viscometer. The rheology sensor 220 may include a rotor 248 that is suspended into the opening 242 of the fluid chamber 218 to make contact and/or be submerged into the drilling fluid sample 230 when the fluid chamber 218 is filled. In some example embodiments, the rotor 248 is an outer cylinder that rotates above a bob (not shown) which is in an inner cylinder. The drilling fluid sample 230 is filled within the annulus between the rotor 248 and the bob. When activated, the rotor 248 rotates at known velocities and creates shear stress on the bob through the drilling fluid sample 230. A torsion spring restrains the movement of the bob and measures the stress. The viscometer may run the tests at any different rotor speed (rotations per minute or RPM). In some cases, the tests are taken at 600, 300, 200, 100, 6 and 3 RPM.

An electric temperature controller may be in communication with the fluid chamber 218. Any appropriate type of electric temperature controller may be used in accordance with the principles described in the present disclosure. In some examples, the electric temperature controller includes a thermoelectric material 256 that has a characteristic of generating an electric current in response to a temperature differential. The thermoelectric material 256 may include a first side 258 in contact with the outside surface 238 of the fluid chamber 218. In some cases, the thermoelectric material 256 includes a second side 260 that is opposite the first side 258 and is in contact with the heat sink 268.

The thermoelectric material 256 may be part of an electric circuit that can pass an electric current through the thermoelectric material 256 to produce both a heated region 262 and a cooled region 264 within the thermoelectric material 256 simultaneously. A polarity switch may be incorporated into the circuit to change the direction that the electric current passes through the thermoelectric material 256. When the electric current passes through the thermoelectric material 256 in a first direction, the heated region 262 is produced adjacent to the fluid chamber 218 and the cooled region 264 is produced adjacent to the heat sink 268. When the heated region 262 is actively produced adjacent to the fluid chamber 218, the electric temperature controller actively controls the temperature of the fluid chamber 218. In some cases, when the heated region 262 is produced adjacent to the fluid chamber 218, the fluid chamber's temperature is raised to a higher temperature, or the fluid chamber's temperature may be maintained to be at a desired temperature for executing a test on the drilling fluid sample 230. In situations when the electric current passes through the thermoelectric material 256 in a second direction that is opposite of the first direction, the heated region 262 is produced adjacent to the fluid chamber 218, and the heated region 262 is produced adjacent to the heat sink 268. In those situations where this cooled region 264 is actively produced adjacent to the fluid chamber 218, the drilling fluid sample 230 temperature is lowered to a cooler temperature, or the drilling fluid sample 230 temperature may be maintained to be at a desired temperature for executing a test on the drilling fluid sample 230.

Figure 5:
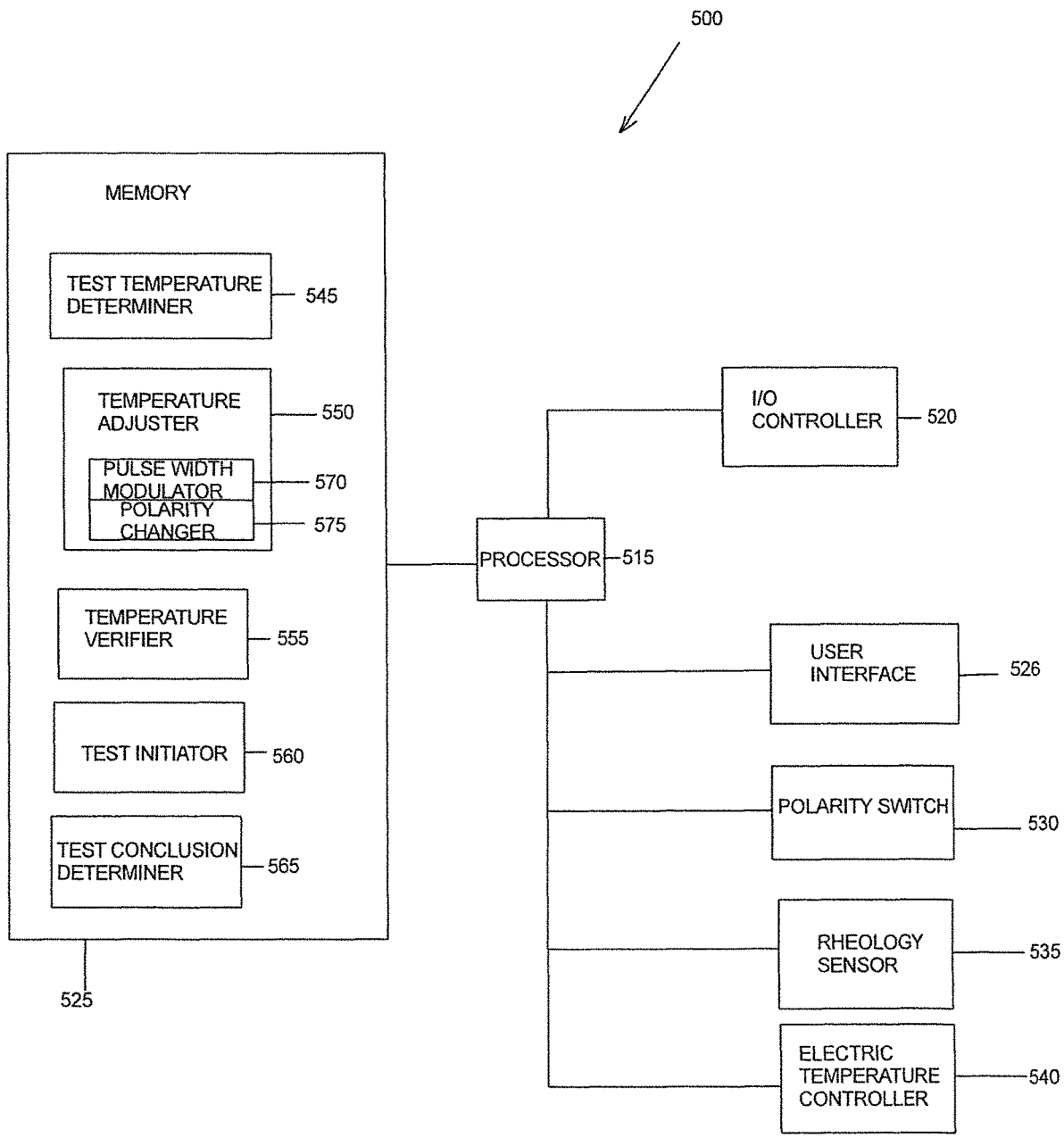
FIG. 5 depicts a diagram of a system for adjusting a temperature of fluid samples in accordance with the present disclosure.

The temperature of the heated region 262 and the cooled region 264 may be controlled with a pulse width modulator 570, as illustrated in FIG. 5. The pulse width modulator 570 may switch the electric current on and off at a frequency rate that produces an average current flow. The longer the pulse width modulator causes electric current to flow through the thermoelectric material 256 compared to the periods where the flow of electric current is stopped, the higher the total power supplied to the thermoelectric material 256, resulting in a higher temperature being produced in the heated region 262 and a lower temperature in the cooled region 264. The difference in temperatures between the heated region 262 and the cooled region 264 may be lowered by increasing the periods of time that the electric current is stopped from flowing through the thermoelectric material 256. The pulse width modulator 570 may cause the thermoelectric material 256 to adjustably heat or cool the fluid chamber 218 to each of the desired temperatures for each of the tests that are to be performed with the fluid chamber 218.

The fluid chamber 218 may be made of a thermally conductive material that spreads the temperature produced by the first side 258 of the thermoelectric material 256. In these embodiments, the fluid chamber 218 is made of aluminum, but the fluid chamber 218 may be made of other types of thermally conductive materials. A non-exhaustive list of thermally conductive materials that may be used to make the fluid chamber 218 includes aluminum, copper, gold, magnesium, beryllium, tungsten, other metals, mixtures thereof, alloys thereof, or combinations thereof. In some cases, the fluid chamber 218 is entirely made of a material that has a substantially consistent thermal conductivity. In some examples, the inside surface of the chamber wall 236 is lined with a material with a different thermal conductivity than other materials that make up a different portion of the fluid chamber 218.

The contact surface 240 of the outside surface 238 of the fluid chamber 218 that is adjacent to the thermoelectric material 256 may include a smooth surface roughness that is in thermal contact with the thermoelectric material 256. In some instances, the contact surface 240 may include a polished surface. Further, in some embodiments, the contact surface 240 includes a smoother finish than other portions of the outside surface 238 of the fluid chamber 218. The smooth finish of the contact surface 240 may reduce gaps between the thermoelectric material 256 and the outside surface 238 of the fluid chamber 218. In some examples, a thermally conductive paste may be used to fill the gaps between the contact surface 240 and the thermoelectric material 256. Even in examples where the contact surface 240 has a smooth finish, the contact surface 240 may still have small gaps that can minimize the thermal transfer between the thermoelectric material 256 and the fluid chamber 218, and the thermally conductive paste may be used in these examples to increase the thermal transfer.

The outside surface 238 of the fluid chamber 218 may be at least partially surrounded with an insulation layer 244. The insulation layer 244 may minimize ambient conditions that would otherwise heat or cool the fluid chamber 218. For example, the insulation layer 244 may prevent an ambient temperature outside of the fluid chamber 218 from heating or cooling the fluid chamber 218 away from the desired temperature for executing a rheology test. In some cases, the insulation layer 244 may prevent the formation of condensation on the outside of the fluid chamber 218 which can cause unwanted cooling of the fluid chamber 218 when bringing the drilling fluid sample 230 to a higher temperature or trying to maintain the drilling fluid sample 230 at a higher temperature.

The fluid chamber 218 may include at least one fluid thermometer 250 that measures the temperature of the drilling fluid sample 230. The fluid chamber 218 may also include at least one equipment thermometer 252 that may measure the temperature of at least one piece of equipment associated with the drilling fluid sample 230. For example, equipment thermometer 252 may measure the temperature of the material forming the fluid chamber 218. Temperature measurements of the fluid chamber material may prevent overheating of the fluid chamber 218.

The heatsink 268 may be constructed from a thermally conductive material and include fins 270 to increase the surface area of the heatsink 268. The fins 270 can be used to exchange temperature with a fluid medium, such as air or a liquid. In examples where the heated region 262 is produced on the second side 260, the heat generated by the heated region 262 can spread throughout the heatsink 268 and be transferred by the fins 270 into the fluid medium. In some cases, a fan 272 is positioned adjacent to the heatsink 268 to cause air to flow through the fins 270 to increase the rate at which heat is dissipated into the air. In other examples, a water or another type of liquid may be passed over the fins 270 as a fluid medium. In this example, the liquid medium does not make contact with the fluid chamber 218, but instead makes contact with the fins 270 of the heatsink 268.

Figure 4:
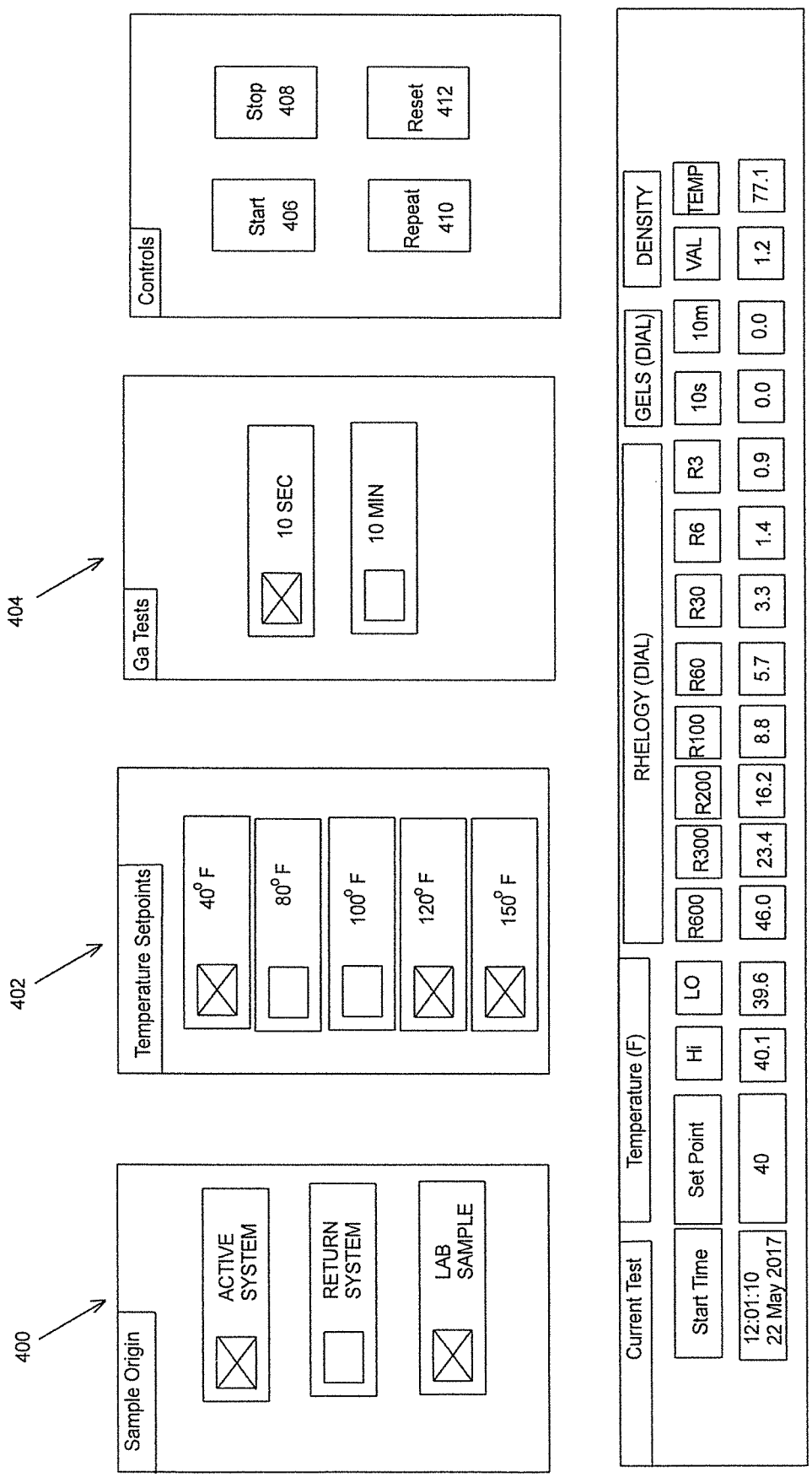
FIG. 4 depicts an example of a user interface of the fluid testing apparatus in accordance with the present disclosure.

FIG. 4 depicts an example of a user interface 104 of the fluid testing apparatus 100 in accordance with many of the embodiments described in the present disclosure. The user interface 104 may also be used with the fluid testing apparatus 900 described in FIG. 9. A user may enter user data into the user interface 104 to instruct the fluid testing apparatus 900 to perform specific tests. This user data may be different for each test performed by the fluid testing apparatus. In this example embodiment, the user interface 104 presents a format for the user to instruct the fluid testing apparatus 100 about performing the tests. In this example, the format includes sample origin options 400 to select the origin of the drilling fluid sample 230, temperature set point options 402 for each of the test, and duration options 404 for each of the tests. Additionally, the user interface 104 presents controls for sending instructions to the fluid testing apparatus 100.

In this example, the user is provided with five temperature set points for performing tests. While the illustrated example depicts five different temperatures for conducting the tests, any appropriate temperature values may be presented to the user as well as any appropriate number of temperature set point options may be presented.

In this example, the test durations are depicted as a 10 second option or a 10 minute option. It will be understood that any appropriate test duration may be presented in accordance with the principles disclosed herein. Further, any appropriate number of test duration options 404 for any presented through the user interface 104.

While the example of FIG. 4 depicts the format presenting a limited number of options that the user can select, in other examples the format presents open fields where the user may specify the values for temperature, test durations, or other testing parameters. Also, some examples may provide the user and ability to add any number of tests to be executed by the fluid testing apparatus 100.

The controls provided in the depicted example include a start command 406, a stop command 408, a repeat command 410, and a reset command 412. The start command 406 may be selected by the user when he or she desires to start the tests. In some examples, in response to sending the start command 406, the fluid testing apparatus executes each of the tests in a sequence without having to have additional involvement from the user. In some examples, the testing sequence includes performing the first test at the lowest selected temperature set point and performing the second test at the second lowest selected temperature set point and so forth until the final test is performed at the highest selected temperature set point. In FIG. 4, a touch capacitive screen or physical buttons may be used.

FIG. 5 depicts a diagram of an electrical system 500 for testing drilling fluid samples. The electrical system 500 may be used with the embodiment described in FIG. 1, or with the embodiment described in FIG. 9. The electrical system 500 may be built within the user interface 104 to allow for compact packing of the related systems. The system 500 includes a processor 515, an I/O controller 520, memory 525, a user interface 526 (that may be the user interface 104), a polarity switch 530, a rheology sensor 535, and an electric temperature controller 540. These components may communicate wirelessly, through hard wired connection, or combinations thereof. The memory 525 of the system 500 may include a test temperature determiner 545, a temperature adjuster 550, a temperature verifier 555, a test initiator 560, and a test conclusion determiner 565. The temperature adjuster 550 includes a pulse width modulator 570, and a polarity changer 575.

The processor 515 may include an intelligent hardware device (e.g. a general purpose processor, a digital signal processor (DSP), a central processing unit (CPU), a microcontroller, an application specific integrated circuit (ASIC), a field-programmable gate array (FPGA), a programmable logic device, a discrete gate or transistor logic component, a discrete hardware component, or any combination thereof. In some cases, the processor 515 may be configured to operate a memory array using a memory controller. In other cases, a memory controller may be integrated into the processor 515. The processor 515 may be configured to execute computer readable instructions stored in a memory to perform various functions. In some embodiments, the processor 515 may be configured to provide instructions to equipment to start or stop, such as the pump 200 or pumps described in FIG. 9.

The I/O controller 520 may represent or interact with a modem, a keyboard, a mouse, a touchscreen, or similar device. In some cases, the I/O controller 520 may be intimated as part of the processor. In some cases, a user may interact with the system via the I/O controller 520 or via hardware components controlled by the I/O controller 520. The I/O controller 520 may be in communication with any appropriate input and any appropriate output.

The memory 525 may include random access memory (RAM) and read only memory (ROM). The memory 525 may store computer readable, computer executable software including instructions that, when executed, cause the processor to perform various functions described herein. In some cases, the memory 525 may contain, among other things, a basic input/output system (BIOS) which may control basic hardware and/or software operation such as the interaction with peripheral components or devices.

The test temperature determiner 545 represents programmed instructions that cause the processor 515 to determine the temperature at which a test is to be performed. In some examples, the test temperature is determined by accessing information the user inputted into the user interface 526.

The temperature adjuster 550 represents programmed instructions that cause the processor 515 to adjust the temperature of the drilling fluid sample 230. Part of the process of adjusting the temperature may include determining the current temperature of the drilling fluid sample and determining whether the desired temperature for the next test is higher or lower than the current temperature of the drilling fluid sample 230. Based on whether the temperature of the drilling fluid sample 230 is to be increased or decreased, the polarity changer 575 may cause the processor 515 to send an instruction to the polarity switch 530 to direct electric current through the thermoelectric material 256 in the appropriate direction. The pulse width modulator 570 may send an instruction to the electric temperature controller 540 to adjust the strength of the electric current to run through the thermoelectric material 256. When the temperature of the drilling fluid sample is being actively changed, the pulse width modulator 570 may cause the signal strength to be greater than when the signal strength is intended to just maintain the drilling fluid sample 230 at its current temperature for testing.

Temperature verifier 555 represents programmed instructions that cause the processor 515 to determine the current temperature of the drilling fluid sample 230. This information can be consulted by the temperature adjuster 550 to determine when to change the signal strength from actively changing the temperature of the drilling fluid sample 230 to maintaining the temperature of the drilling fluid sample 230.

The test initiator 560 represents programmed instructions that cause the processor 515 to cause the test to be performed with the rheology sensor 535. The test initiator 560 may also consult information from the temperature verifier 555 to determine if the drilling fluid sample is at the appropriate temperature for executing the test.

The test conclusion determiner 565 represents programmed instructions that cause the processor 515 to determine when a test is completed. In some examples, the test conclusion determiner 565 sends a signal to the temperature adjuster 550 at the conclusion of a test at a first temperature. In response, the temperature adjuster 550 may start the process for changing the temperature of the drilling fluid sample 230 for the next test in a different desired temperature.

Figure 6:
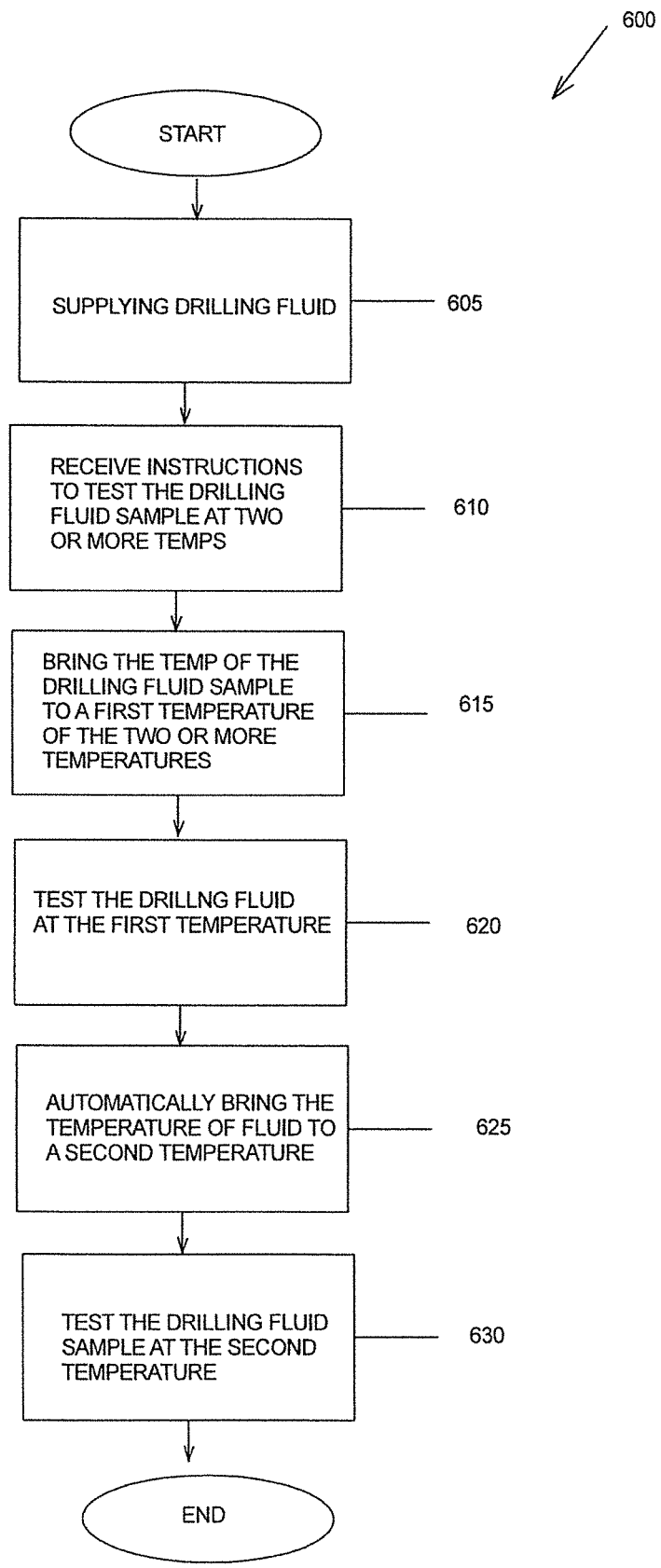
FIG. 6 depicts an example of a method for automated testing of a fluid sample at different temperatures in accordance with the present disclosure.

FIG. 6 depicts an example of a method 600 for automating testing of the fluid samples at different temperatures in accordance with the present disclosure. In this example, the method 600 includes supplying 605 a drilling fluid sample 230 into a fluid chamber 218, receiving 610 instructions to test the drilling fluid sample 230 at two or more temperatures, bringing 615 the temperature of the drilling fluid sample 230 to a first temperature of the two or more temperatures through the fluid chamber with an electric temperature controller, testing 620 the drilling fluid sample 230 at the first temperature with a rheology sensor incorporated into the fluid chamber, automatically bringing 625 the temperature of the drilling fluid sample 230 to a second temperature after a conclusion of the test at the first temperature with the electric temperature controller, and testing 630 the drilling fluid sample 230 at the second temperature with the rheology sensor. At least some of the portions of this method may be carried out in accordance with the principles described in the present disclosure.

Figure 7:
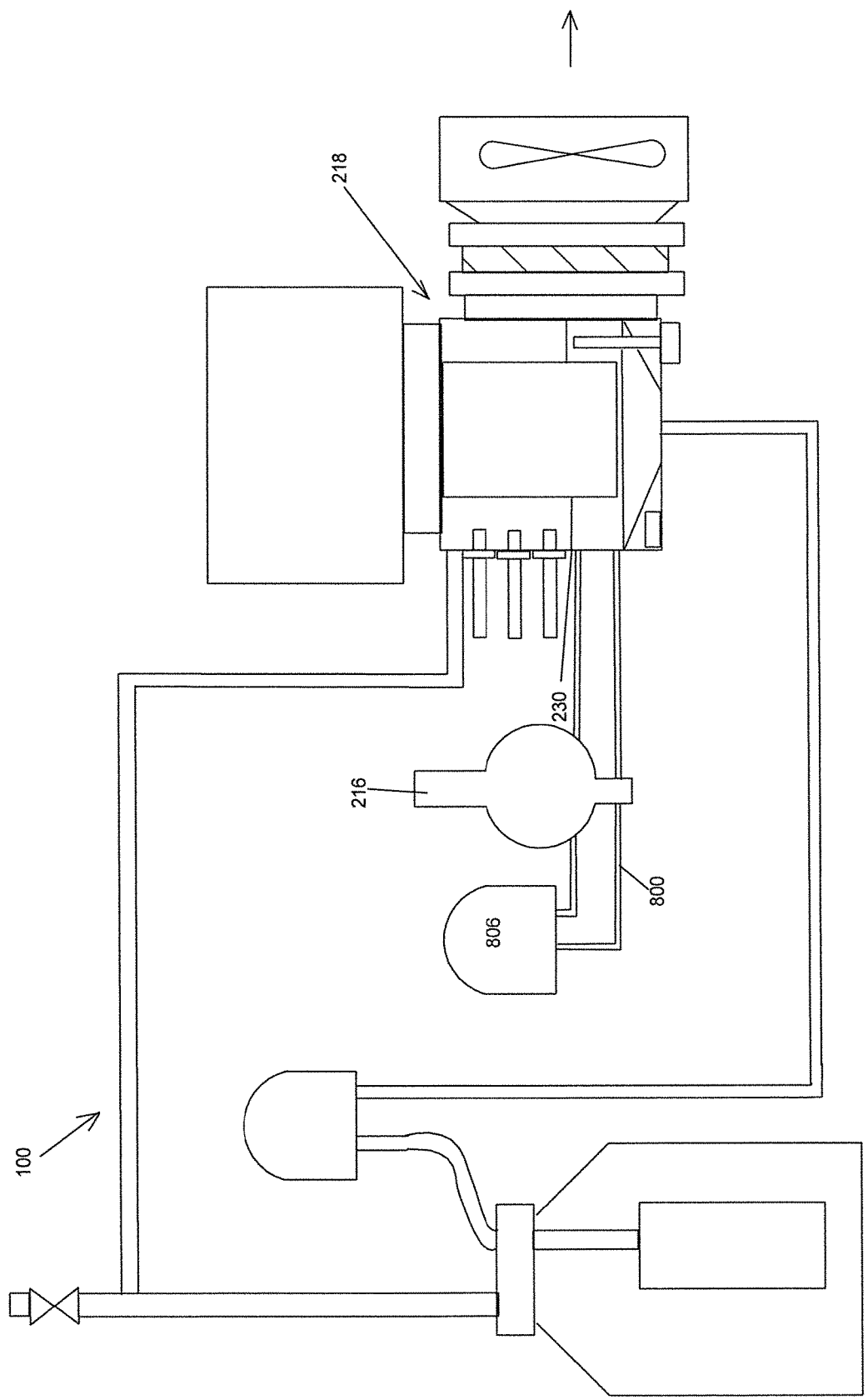
FIG. 7 depicts an example of components of a fluid testing apparatus with a side loop for controlling temperature of fluid for density measurements in accordance with the present disclosure.

FIG. 7 depicts an example of components of the fluid testing apparatus 100 with a side loop 800 for controlling a temperature of the fluid for density measurements in accordance with the present disclosure. In the depicted example, a side loop 800 is incorporated into the fluid testing apparatus 100. A second pump 806 and the density sensor 216 is incorporated into the side loop 800. The second pump 806 may cause a portion of the drilling fluid sample 230 to enter into the side loop 800 from the fluid chamber 218 when the drilling fluid is at a desired temperature for testing the density of the drilling fluid sample 230.

Figure 8:
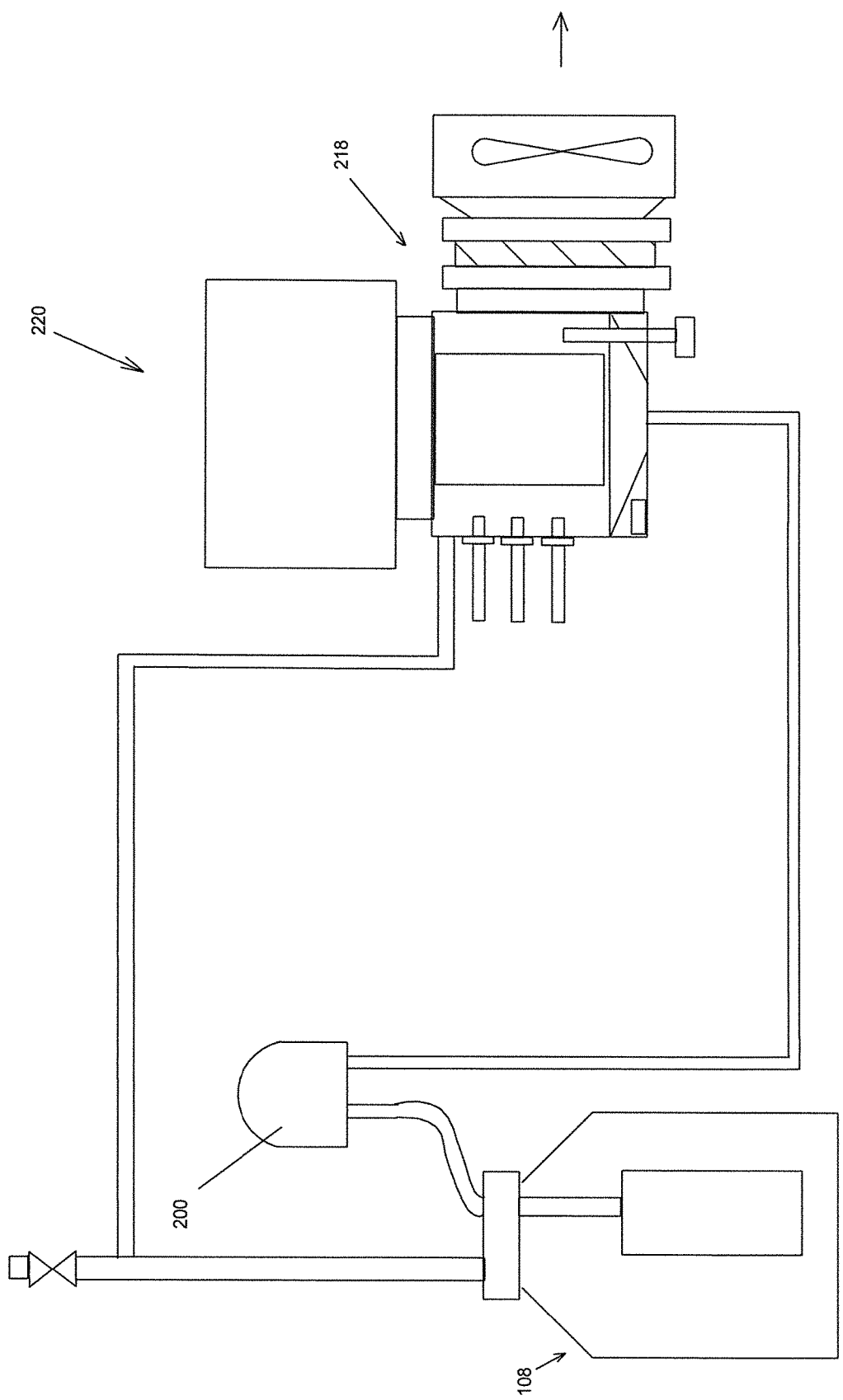
FIG. 8 depicts an example of components of a fluid testing apparatus without a density sensor in accordance with the present disclosure.

In some examples, the user interface presents the user with options to test the rheology of the drilling fluid sample 230, to test the density of the drilling fluid sample 230, or combinations thereof. The user may instruct the fluid testing apparatus 100 to test the drilling fluid sample 230 at the same temperature at which the rheology sensor 220 tests the drilling fluid sample 230. In other examples, the density of the drilling fluid sample 230 may be tested at a temperature that is different from at least one of the tests conducted with the rheology sensor 220. In some cases, the electric heating controller brings the drilling fluid sample 230 to a temperature for tests performed by either the rheology sensor 220, the density sensor 216, another type of sensor incorporated into the fluid chamber 218, or combinations thereof. In the example of FIG. 8, the fluid testing apparatus 100 does not include a density sensor 216 in accordance with the present disclosure.

Figure 9:
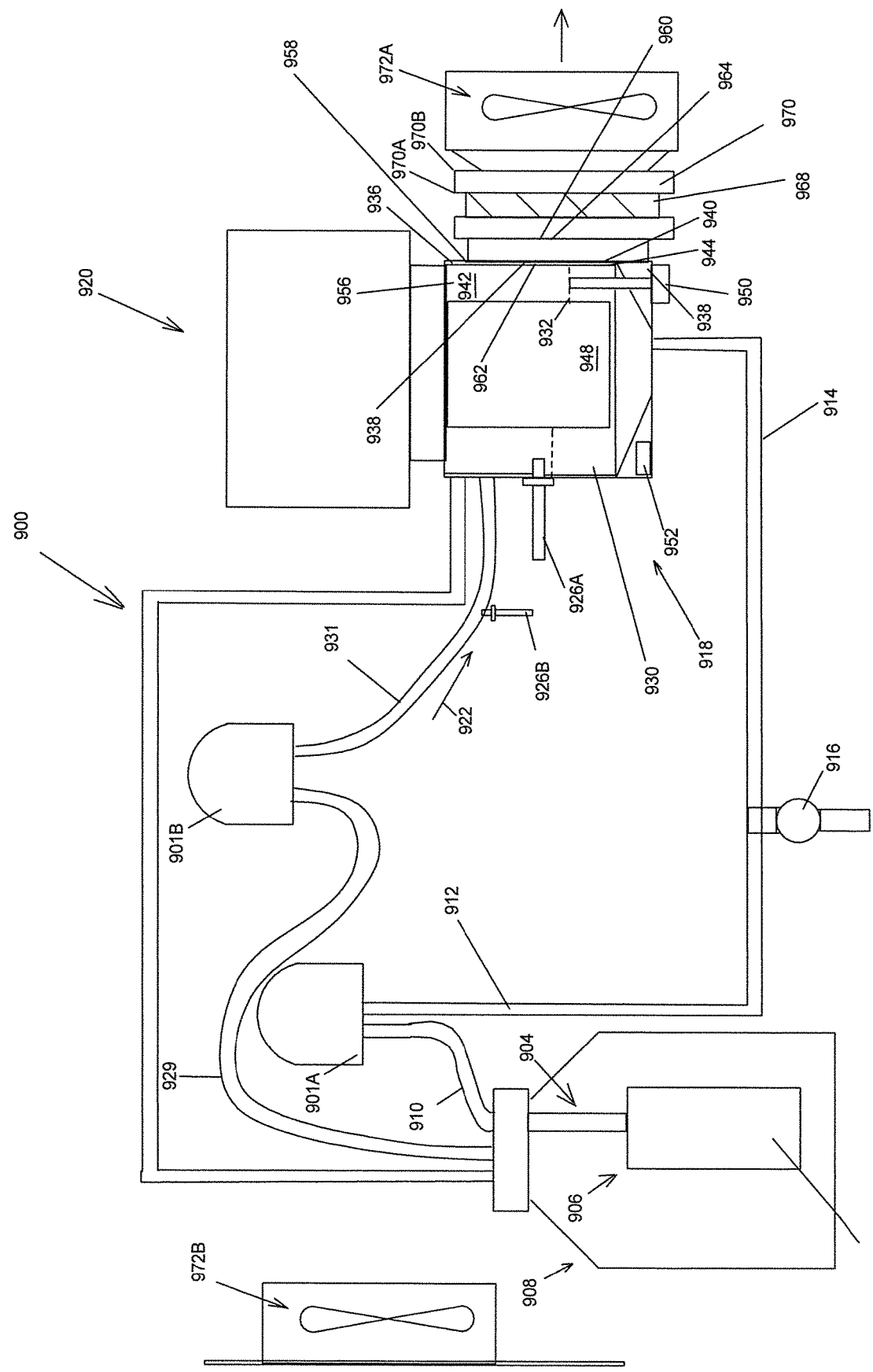
FIG. 9 depicts a two-pump automated fluid testing apparatus in accordance with the present disclosure.
Figure 9A:
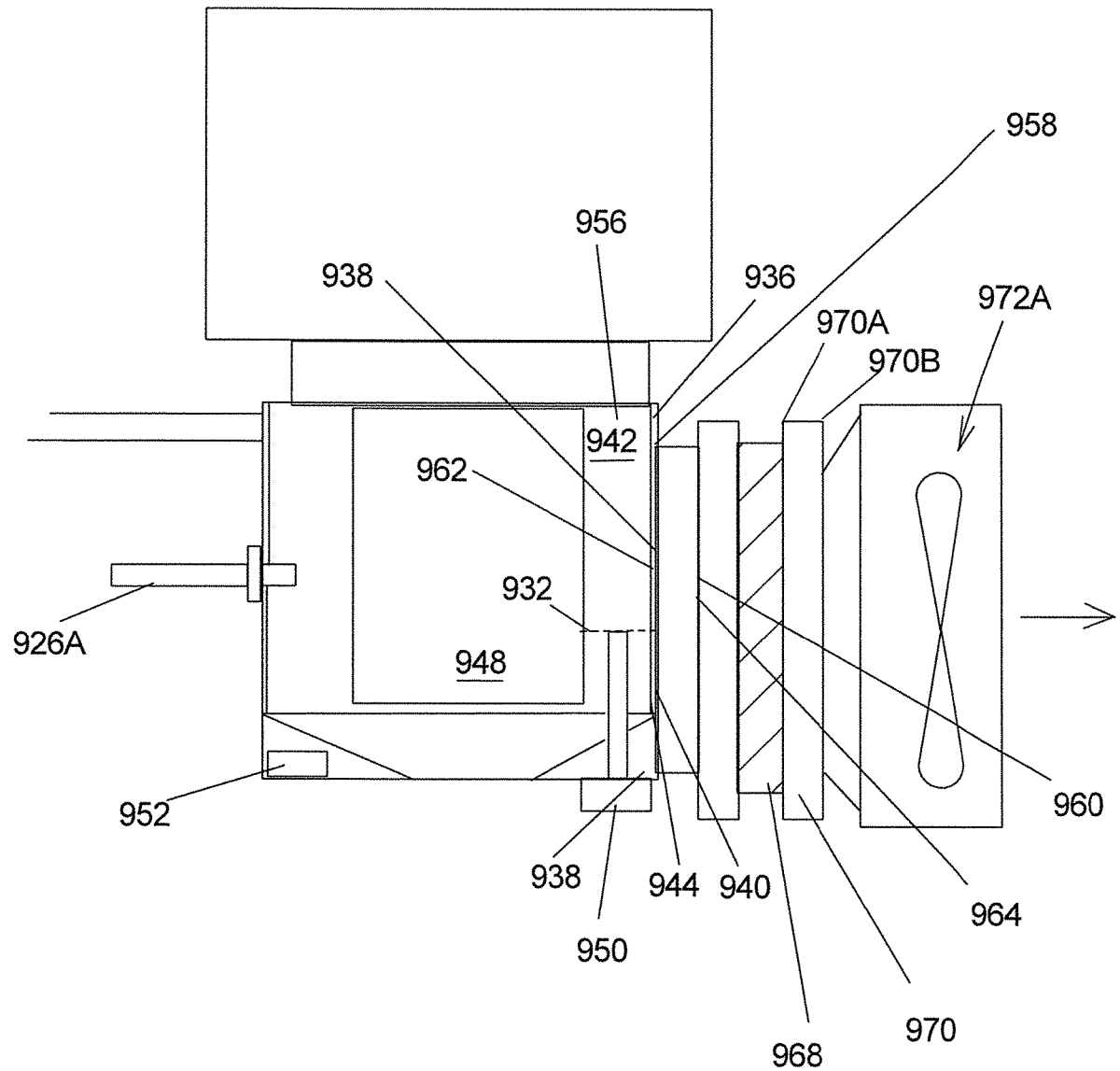
FIG. 9A depicts an enlarged view of the automated fluid testing apparatus of FIG. 9.

Referring to FIGS. 9 and 9A, a two pump automatic fluid measuring apparatus 900 is disclosed. As in previous embodiments, a drilling fluid sample 930 may be held within a bottle. In this example, the fluid testing apparatus 900 includes a bottle receiver 906, a first pump 901A, a second pump 901B, a fluid conduit 904, a density sensor 916 connected to the fluid conduit 904, a fluid chamber 918, and a rheology sensor 920 connected to the fluid chamber 918.

In this embodiment, two pumps 901A and 901B are provided for moving fluid through the attached systems rather than a single pump 200 as described in FIG. 2. In the embodiment of FIGS. 9 and 9A, rheology measurements are taken through use of a rheology sensor 920. Similar to FIG. 2, the rheology sensor 920 may be a viscometer, in one embodiment. The use of two pumps 901A and 901B allows for drilling fluids to be tested at quicker intervals compared to a single pump unit, and the presence of pump 901B allows for ensuring that the fluid chamber 918 is not overfilled during filling cycles. Draining and refilling of the fluid chamber 918 may take place at a greater rate than using mere gravity means for evacuation of fluids. The use of two pumps 901A and 901B also adds redundancy to the testing apparatus 900 compared to single pump units, allowing for greater availability of the unit. In embodiments, pump 901B may be run at a higher speed than pump 901A. In this instance, the presence of pump 901B prevents overfilling of fluid chamber 918. The pump 901A may be controlled to turn off if pump 901B encounters fluid being pumped through the fluid conduit to the fluid chamber 918. In other embodiments, sensors in the fluid chamber 918, or near the fluid chamber 918, may be used to switch off pump 901A to prevent overfilling.

The rheology sensor 920 may include a rotor 948 that is suspended into the opening 942 of the fluid chamber 918. The rotor 948 makes contact with the drilling fluid sample 930 through full or partial submersion. In one embodiment, the rotor 948 has an outer cylinder that rotates above a bob (not shown) which is placed within an inner cylinder. The drilling fluid sample 930 is filled within the annulus between the rotor 948 and the bob. A motor may drive the rotor 948. The motor may be a variable speed motor that may be controlled through the actions of a user. Through control of the motor, the rotor 948 rotates at known velocities and creates shear stress on the bob as the bob contacts the drilling fluid sample 930. A torsion spring measures the stress exerted by the fluid on the bob. The rheology sensor 920 may run tests at different rotor speeds (rotations per minute or RPM). In some cases, the tests are taken at 600, 300, 200, 100, 6, and 3 RPM. Other values of rotor speed may be used. The rotation of the bob within the drilling fluid sample 930 at such values is not possible in conventional units when the drilling fluid is especially gelatinous. To this end, the testing apparatus 900 is provided with a high duty motor that allows for rotations of the bob experiencing high sheer stress.

An electric temperature controller, as provided in the electric system 500, as described in FIG. 5, is used to heat or cool the fluid chamber 918 that contains the drilling fluid sample 930. Any type of electric temperature controller 540 may be used in accordance with the principles described in the present disclosure. In some examples, the electric temperature controller 540 includes a thermoelectric material 956 that generates an electric current in response to a temperature differential. In this embodiment, the thermoelectric material 956 has a first side 958 in contact with the outside surface 938 of the fluid chamber 918. In some embodiments, the thermoelectric material 956 may include a second side 960 that is opposite the first side 958 and is in contact with the heat sink 968.

In some embodiments, the thermoelectric material 956 is part of an electric circuit that is used to either heat or cool the drilling fluid sample 930. Electric current is passed through the thermoelectric material 956 to produce, simultaneously, both a heated region 962 and a cooled region 964 within the thermoelectric material 956. In some embodiments, a polarity switch, located in the electric system 500, may be installed within the electric circuit to change a direction that the electric current passes through the thermoelectric material 956. When the electric current passes through a thermoelectric material 956 in a first direction, a heated region 962 is produced. This heated region 962 is located adjacent to the fluid chamber 918. At the same time, a cooled region 964 is also produced adjacent to the heat sink 968. When the heated region 962 is actively produced adjacent to the fluid chamber 918, the electric temperature controller 540 actively keeps the fluid chamber 918 at a specified temperature. In some embodiments, when the heated region 962 is produced adjacent to the fluid chamber 918, the fluid chamber's temperature is raised to a higher temperature, or the fluid chamber's temperature may be maintained to be at a desired temperature for executing a test on the drilling fluid sample 930. In situations when the electric current passes through the thermoelectric material 956 in a second direction that is opposite of the first direction, the heated region 962 is produced adjacent to the fluid chamber 918, and the heated region 962 is produced adjacent to the heat sink 968. In situations where the cooled region 964 is produced adjacent to the fluid chamber 918, the drilling fluid sample temperature is lowered to a cooler temperature. In other embodiments, the drilling fluid sample temperature may be maintained at a desired temperature.

In one or more embodiments, a pulse width modulator 570, as provided in electric system 500 may be used to control the temperature of the heated region 962 and the cooled region 964. The pulse width modulator 570 may switch the electric current on and off at a frequency to produce an average current flow within the thermoelectric material 956. In an example embodiment, the longer the pulse width modulator 570 causes the electric current to flow through the thermoelectric material 956 compared to the periods where the flow of electric current is stopped, the higher the total electrical power supplied to the thermoelectric material 956. This higher total electrical power supplied results in a higher temperature being produced in the heated region 962 and a lower temperature in the cooled region 964. The difference in temperatures between the heated region 962 and the cooled region 964 may be lowered by increasing the periods of time that they electric current is stopped from flowing through the thermoelectric material 956. The pulse width modulator 570 may cause the thermoelectric material 956 to adjustably heat or cool the fluid chamber 918 to each of the desired temperatures for each of the tests that are to be performed with the fluid chamber 918.

As with the some embodiments described above, the fluid chamber 918 may be made of a thermally conductive material that spreads the temperature produced by the first side 958 of the thermoelectric material 956. In one embodiment, the fluid chamber 918 is made of aluminum. As will be understood, the fluid chamber 918 may be made of other types of thermally conductive materials. A non-exhaustive list of thermally conductive materials that may be used to make the fluid chamber 918 includes aluminum, copper, gold, magnesium, beryllium, tungsten, titanium, other metals, mixtures thereof, alloys thereof, or combinations thereof. In some embodiments, the fluid chamber 918 is constructed from a substantially consistent thermal conductivity material. In some example embodiments, an inside surface of the chamber wall 936 is lined with a material with a different thermal conductivity than other materials that make up different portions of the fluid chamber 918.

An outside surface 938 is provided on the fluid chamber 918 that is adjacent to the thermoelectric material 956. A contact surface 940 is located on a portion of the outside surface 938. The contact surface 940 may include a smooth surface roughness that is in thermal contact with the thermoelectric material 956. In some embodiments, the contact surface 940 includes a polished surface. In other embodiments, the contact surface 940 includes a smoother finish than other portions of the outside surface 938 of the fluid chamber 918. In an instance where a smooth finish of the contact surface 940 is used, the smooth finish may reduce gaps between the thermoelectric material 956 and the outside surface 938 of the fluid chamber 918. If gaps are present between the contact surface 940 and the thermoelectric material 956, a thermally conductive paste may be used to fill the gaps.

The outside surface 938 of the fluid chamber 918 may be at partially surrounded with an insulation layer 944. The insulation layer 944 may minimize ambient conditions that would otherwise heat or cool the fluid chamber 918.

The fluid chamber 918 may include at least one fluid thermometer 950 that measures the temperature of the drilling fluid sample 930. The fluid chamber 918 may also include at least one equipment thermometer 952 that may measure the temperature of at least one piece of equipment associated with the drilling fluid sample 930. For example, equipment thermometer 952 may measure the temperature of the material forming the fluid chamber 918. Temperature measurements of the fluid chamber's material can prevent overheating of the fluid chamber 918. Data from the at least one equipment thermometer 952 and the at least one fluid thermometer 950 may be monitored through circuitry configured to receive such data inputs. In one embodiment, a level detection sensor may send a signal to the pump 901B to stop pumping in the drilling fluid sample 930 when the fluid level 932 is at an appropriate height.

The heatsink 968 may include fins 970 to increase the surface area of the heatsink 968. The fins may be located on an inside portion 970A and an outside portion 970B. The fins 970 can be used to exchange temperature with a fluid medium, such as air or a liquid. In examples where the heated region 962 is produced on the second side 960, the heat generated by the heated region 962 can spread throughout the heatsink 968 and be transferred through the fins 970 into the fluid medium. In some example embodiments, a fan 972A is positioned adjacent to the heatsink 968 to cause air to flow through the fins 970 to increase the rate at which heat is dissipated into the air. A second fan 972B may also be used to provide cooling within the enclosure that houses the fluid measuring apparatus 900. The presence of the second fan provides superior cooling to configurations where one fan is used. As will be understood, the presence of such fans may limit heat build-up within the fluid measuring apparatus 900, thereby providing a more robust ability to withstand temperature variations.

In other examples, water or another type of liquid may be passed over the fins 970 to provide extra cooling capacity. In this example, the liquid medium does not contact the fluid chamber 918, but instead makes contact with the fins 970 of the heatsink 968. The liquid medium may be, for example, water or an ethylene glycol solution.

In the embodiment of FIG. 9, two pumps 901A and 901B are used to convey fluid within the drilling fluid analyzer. In the embodiment disclosed, the pumps may be peristaltic pumps. One pump 901A is connected to the sample bottle 908, with strainer 902 through first line portion 910 and a density sensor 916 through second line portion 912. A second pump 901B is connected to the sample bottle 908 and the fluid chamber 918 through line 929. The second pump 901B is also connected to the fluid chamber 918 through line 931 with a flow direction 922 indicated. The density sensor 916 is then connected to the fluid chamber 918 through third portion 914. The use of two pumps 901A and 901B allows for sampling of more gelatinous solutions that were previously unable to be sampled and analyzed by conventional analyzers. Different than the other embodiments disclosed, the first pump 901A is closely positioned to both the sample bottle 908 and the density sensor 916, thereby allowing density readings of the fluid sample to be obtained. The density sensor 916, in turn, is connected through a third portion 914 to the fluid chamber 918. The first pump 901A may provide the motive force for moving the fluid sample from the sample bottle 908. Fluid levels within the fluid chamber 918 are measured through first level detector 926A. A second level detector 926B is located in the line from the second pump 901B to the fluid chamber 918. The density sensor 916 in FIG. 9 may be a Rheonik Model RHM04. At the conclusion of testing, fluid may be returned to the bottle for storage. Data obtained during the testing may be transmitted by either a wired or a wireless connection to a computer for review by engineering personnel. In embodiments, data may be supplied through a WITS protocol or to a GN5 data acquisition system by Geoservices, a Schlumberger Company. As will be understood, wired connections may be Ethernet communication enabled.

In other embodiments, warnings of overfilled conditions or degraded components of the fluid measuring apparatus 900 may be provided wirelessly or through a wired connection to allow engineering personnel to monitor ongoing evaluations. In the embodiments shown in FIG. 1 and FIG. 9, the memory, in electric system 500 provided may non-volatility store data from tests conducted.

Figure 10:
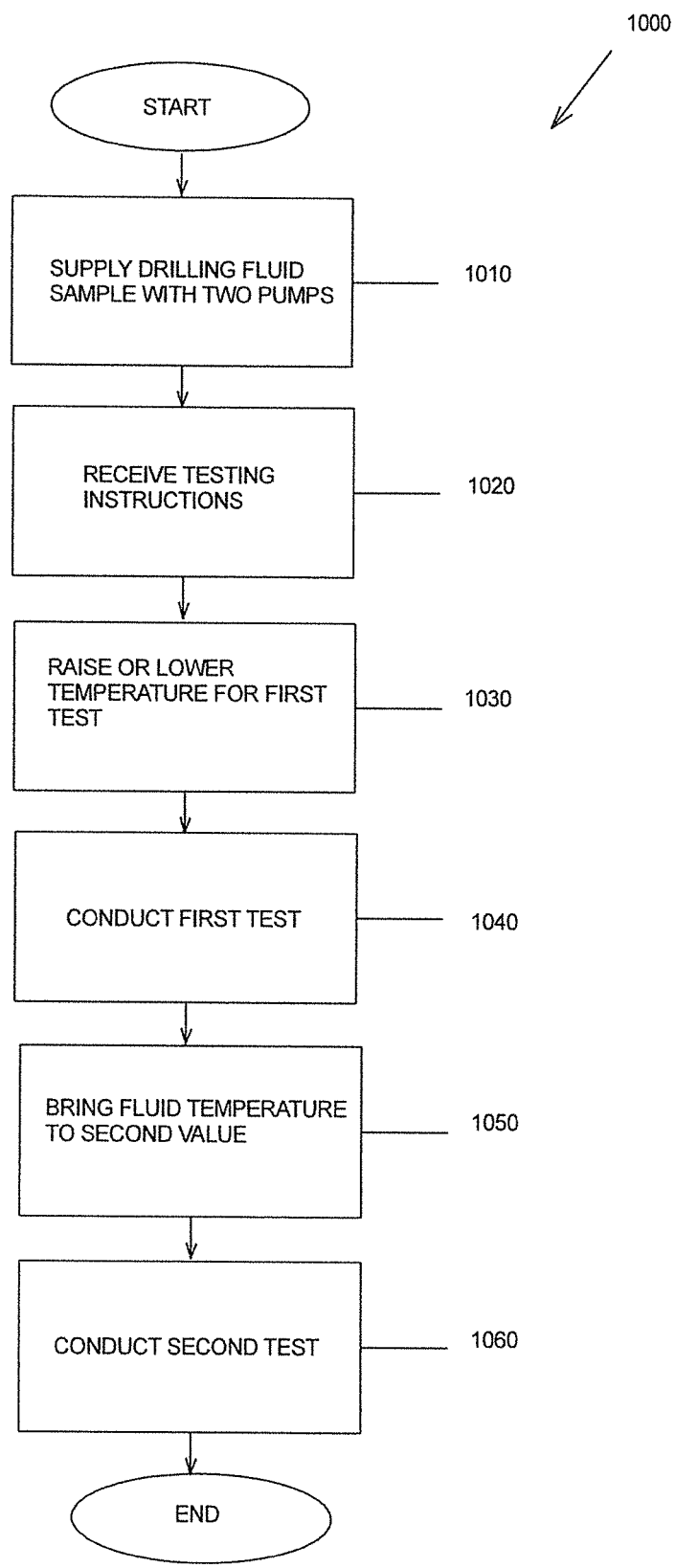
FIG. 10 depicts a method for automated testing of a fluid sample with a two-pump automated fluid testing apparatus in accordance with the present disclosure.

Referring to FIG. 10, an example of a method 1000 for automating testing of the fluid samples at different temperatures is disclosed in accordance with the present disclosure. In this example, the method 1000 includes supplying 1010 a drilling fluid sample into a fluid chamber through action of two pumps. In this supplying 1010, the first pump 901A may supply the fluid to the fluid chamber 918, and the second pump 901B may remove excess fluid sample from accumulating within the fluid chamber 918. This ensures that a proper amount of fluid enters the fluid chamber 918 for testing. At 1020, the method continues with receiving instructions to test the drilling fluid sample at two or more temperatures. At 1030, the method continues by one of raising and lowering a temperature of the drilling fluid sample to a first temperature of the two or more temperatures through a fluid chamber. The raising or lowering may be performed through an electric circuit. The method continues at 1040 by testing the drilling fluid sample at the first temperature with a rheology sensor 535 incorporated into the fluid chamber. The method continues at 1050 by automatically bringing the temperature of the drilling fluid sample to a second temperature after a conclusion of the test at the first temperature. The method continues at 1060 with testing the drilling fluid sample at the second temperature with the rheology sensor 535. At least some of the portions of this method may be carried out in accordance with the principles described in the present disclosure.

While the fluid testing apparatus has been described above as having a bottle receiver for connection to a bottle containing the drilling fluid sample, in some examples, no bottle receiver is incorporated into the fluid testing apparatus. For example, the user may pour the drilling fluid sample into a tank incorporated into the fluid testing apparatus. In some examples, where the drilling fluid sample is incorporated into the fluid testing apparatus, a filter may be incorporated into an outlet of the tank to filter out sand, debris, other types of solids, or combinations thereof. In some cases, the user may pour the drilling fluid sample directly into the fluid chamber connected to the viscometer or other rheology sensor. As will be understood, the field-testing apparatus 100, 900 may be mobile such that a user may take the apparatus 100, 900 to different site locations. In embodiments, a battery pack may be provided to provide the needed electrical current to run the apparatus 100, 900. In other embodiments, the housing 102 may have an electrical cord to plug the apparatus 100, 900 into the electrical system of a drilling rig.

In the embodiments described, the automated analysis of drilling fluid may be performed over long periods of time. In some embodiments, the analyzer may conduct analysis of drilling fluid between 2 to 6 days without need for cleaning. Cleaning of the insides of the analyzer may be accomplished without running a demineralized water solution through the analyzer. In a sample cleaning routine, fluids within the analyzer may be heated to a specified value to allow for draining and cleaning of the analyzer parts. As will be understood, in the embodiment provided in FIG. 9, either of the pumps 901A or 901B may be used to provide motive force for the fluid within the apparatus 100, 900. In one embodiment, a single pump, either pump 901A or 901B, may be used to drive drilling fluid in a first direction. After a first pump run cycle, an alternative pump 901B may be used to drive drilling fluid in a second direction, wherein the second direction is opposite of the first direction. The alternative pump 901B may then be run for a second pump run cycle.

In embodiments described, the use of heat sinks and multiple fans may allow for increases or decreases in temperature of 30 degrees Celsius over a five (5) minute time frame.

The foregoing description, for purpose of explanation, has been described with reference to specific embodiments. However, the illustrative discussions above are not intended to be exhaustive or to limit the disclosure to the precise forms disclosed. Many modifications and variations are possible in view of the above teachings. The embodiments were chosen and described in order to best explain the principles of the present systems and methods and their practical applications, to thereby enable others skilled in the art to best utilize the present systems and methods and various embodiments with various modifications as may be suited to the particular use contemplated.

What is claimed is:
1. A testing apparatus, comprising:
 a fluid collection container configured to hold a drilling fluid;
 a first fluid conduit connected to the fluid collection container;
 a second fluid conduit connected to the fluid collection container;
 a fluid chamber configured to receive the drilling fluid from both the first fluid conduit and the second fluid conduit;
 a first pump configured to move the drilling fluid from the fluid collection container to the fluid chamber, the first pump connected to the first fluid conduit;
 a second pump configured to move the drilling fluid from the fluid collection container to the fluid chamber, the second pump connected to the second fluid conduit;
 a rheology sensor in communication with the fluid chamber;
 a user interface configured to accept user defined data; and
 an electrical system connected to the user interface and configured to process the user defined data,
 wherein the testing apparatus is configured to receive user data on tests to be performed by the testing apparatus, and control the first pump, the second pump and the rheology sensor to automatically test the drilling fluid according to the user defined data; further comprising:

an electric circuit configured to at least one of heat and cool the drilling fluid within the fluid chamber and wherein the electrical system further comprises an electric temperature controller pulse modulator configured to generate a control signal to control the electric circuit;

wherein the electric circuit further comprises:

a thermoelectric material placed on an outside surface of the fluid chamber; wherein a current is passed through the thermoelectric material to produce both a heated region and a cooled region on opposite sides of the thermoelectric material.

2. The testing apparatus of claim 1, wherein the electric circuit is configured to both heat and cool the fluid chamber housing the fluid sample.

3. The testing apparatus of claim 1, further comprising:

at least one thermometer connected to the electrical system and configured to obtain a fluid temperature within the fluid chamber.

4. The testing apparatus of claim 1, further comprising:

a filter positioned inside the fluid collection container, wherein at least one of the first fluid conduit and the second fluid conduit connects to the filter.

5. The testing apparatus of claim 1, further comprising:

at least one level detector connected to the fluid chamber and configured to measure a level of fluid within the fluid chamber when fluid is present.

6. The testing apparatus of claim 1, wherein the user interface is a capacitive screen.

7. The testing apparatus of 1, further comprising:

a housing configured to house the first fluid conduit, the second fluid conduit, the fluid chamber, the first pump, the second pump, the rheology sensor, the electrical system, and the user interface.

8. The testing apparatus of claim 7, further comprising:

at least two fans configured to move air through the housing.

9. The testing apparatus of claim 1, wherein the rheology sensor is a viscometer.

10. A method for automatic testing fluid samples, comprising:

supplying a drilling fluid sample into a fluid chamber through action of at least two pumps;

receiving instructions to test the drilling fluid sample for at least two temperatures;

automatically adjusting a temperature of the drilling fluid sample to a first temperature of the at least two temperatures through the fluid chamber with an electric temperature controller;

testing the fluid sample at the first temperature; wherein the testing of the fluid sample is carried out with a rheology sensor incorporated into the fluid chamber;

automatically adjusting the temperature of the drilling fluid sample to a second temperature of the at least two temperatures; and testing the fluid sample at the second temperature.

11. The method of claim 10, wherein the rheology sensor is a viscometer.

12. The method of claim 10, wherein the drilling fluid sample is supplied directly from a drilling operation.

13. A testing apparatus, comprising:

a fluid collection container configured to hold a drilling fluid;

a first fluid conduit connected to the fluid collection container;

a second fluid conduit connected to the fluid collection container;

a fluid chamber configured to receive the drilling fluid from the fluid conduits;

a first pump configured to move the drilling fluid from the fluid collection container to the fluid chamber;

a second pump configured to move the drilling fluid from the fluid collection container to the fluid chamber;

a rheology sensor in communication with the fluid chamber;

a user interface configured to accept user defined data;

an electrical system connected to the user interface and process the user defined data, wherein the testing apparatus is configured to receive user data, and control the first pump, the second pump and the rheology sensor to automatically test the drilling fluid according to the user defined data, the electrical system further configured with a memory to store and transmit data related to parameters of a tested fluid;

at least two fans configured to move a volume of air;

at least one equipment thermometer connected to at least one of the rheology sensor, the first pump and the second pump; and a housing configured to house the first pump, the second pump, the rheology sensor, the user interface, the electrical system, the at least one equipment thermometer and the at least two fans.

14. The testing apparatus of claim 13, wherein the rheology sensor is a viscometer.

15. The testing apparatus of claim 14, wherein the fluid chamber is a component of the viscometer.

16. The testing apparatus of claim 13, wherein the electrical system is configured with a processor configured to perform the processing of the user defined data and a non-volatile memory configured to store data obtained from the processor and the user interface.

* * * * *